(12) United States Patent
Rogel et al.

(10) Patent No.: US 9,285,241 B2
(45) Date of Patent: Mar. 15, 2016

(54) DEVICES, SYSTEMS, AND METHODS FOR GAMES, SPORTS, ENTERTAINMENT AND OTHER ACTIVITIES OF ENGAGEMENT

(75) Inventors: Lawrence S. Rogel, Brookline, MA (US); Jason J. Ossenmacher, Mission Viejo, CA (US); Jon Williams, Cambridge, MA (US); David Witmer, Boston, MA (US); Matt Garcia, Cambridge, MA (US)

(73) Assignee: Intellisys Group, LLC, Boston, MA (US)

( * ) Notice: Subject to any disclaimer, the term of this patent is extended or adjusted under 35 U.S.C. 154(b) by 714 days.

(21) Appl. No.: 13/565,966

(22) Filed: Aug. 3, 2012

(65) Prior Publication Data
US 2013/0083941 A1  Apr. 4, 2013

Related U.S. Application Data

(63) Continuation-in-part of application No. PCT/US2011/046423, filed on Aug. 3, 2011, and a continuation of application No. 13/197,429, filed on Aug. 3, 2011.

(Continued)

(51) Int. Cl.
*A63F 13/54* (2014.01)
*G06F 17/40* (2006.01)
(Continued)

(52) U.S. Cl.
CPC ............. *G01C 23/00* (2013.01); *A63C 17/26* (2013.01); *H04R 1/02* (2013.01); *A63C 17/01* (2013.01);
(Continued)

(58) Field of Classification Search
CPC .... A63B 69/00; A63B 69/0022; A63B 71/00; A63B 71/06; A63B 2220/00; A63B 2220/10; A63B 2220/40; A63B 2220/80; A63B 2220/803; A63C 17/00; A63C 17/01; A63C 17/26; A63C 2203/00; A63C 1103/18; A63C 2203/24; A63F 13/00; A63F 13/005; A63F 13/06; A63F 13/25; A63F 13/28; A63F 13/50; A63F 13/54; A63F 2300/00; A63F 1300/10; A63F 2300/25; A63F 2300/1031; A63F 2300/1043; A63F 2300/105; A63F 2300/1087; A63F 2300/20; A63F 2300/205; A63F 2300/30; A63F 2300/301; A63F 2300/80; A63F 2300/8041; G01C 9/00; G01C 23/00; G01D 7/00; G01D 9/00; G01D 21/00; G06F 11/00; G06F 11/30; G06F 11/32; G06F 11/34; G06F 15/00; G06F 15/16; G06F 17/00; G06F 17/10; G06F 17/40; G06F 19/00; G10K 15/00; G10K 15/02; H04R 1/00; H04R 1/02; G10L 13/00; H04W 88/00; H04W 88/02
USPC ............. 73/432.1, 488, 489, 495, 510, 865.4, 73/865.8, 865.9, 866.3; 273/440, 454; 340/384.1, 500, 540, 665; 381/86; 463/1, 7; 702/1, 33, 41, 127, 150, 182, 702/187, 189; 708/100, 105, 200
See application file for complete search history.

(56) References Cited

U.S. PATENT DOCUMENTS 4,074,903 A   2/1978  Diez de Aux
4,502,035 A * 2/1985  Obenauf et al. .......... 340/323 R
(Continued)

OTHER PUBLICATIONS

[No Author] Bump KickFlick! Solderin' Skaters. Retrieved Nov. 17, 2011 from solderinskaters.net. Photograph (2 Pages).
(Continued)

*Primary Examiner* — Edward Cosimano
(74) *Attorney, Agent, or Firm* — Nutter McClennen & Fish LLP; David J. Powsner

(57) ABSTRACT

Devices, systems, and methods according to one such aspect of the invention comprises (i) a sensing device that is attached (or otherwise coupled) to a skateboard and that measures a physical characteristic of it and/or of its environment, (ii) an audio output device, and (iii) a digital data processor that is communicatively coupled to the audio output device and the sensor. The digital data processor drives the audio output device to effect one or more selected sounds (e.g., to prompt the user to perform a selected action). The digital data processor, further, and monitors the sensing device to identify user actions in response to those sounds and drives the audio output device to effect still further sounds based on those actions.

17 Claims, 4 Drawing Sheets

Related U.S. Application Data

Figure 1A:
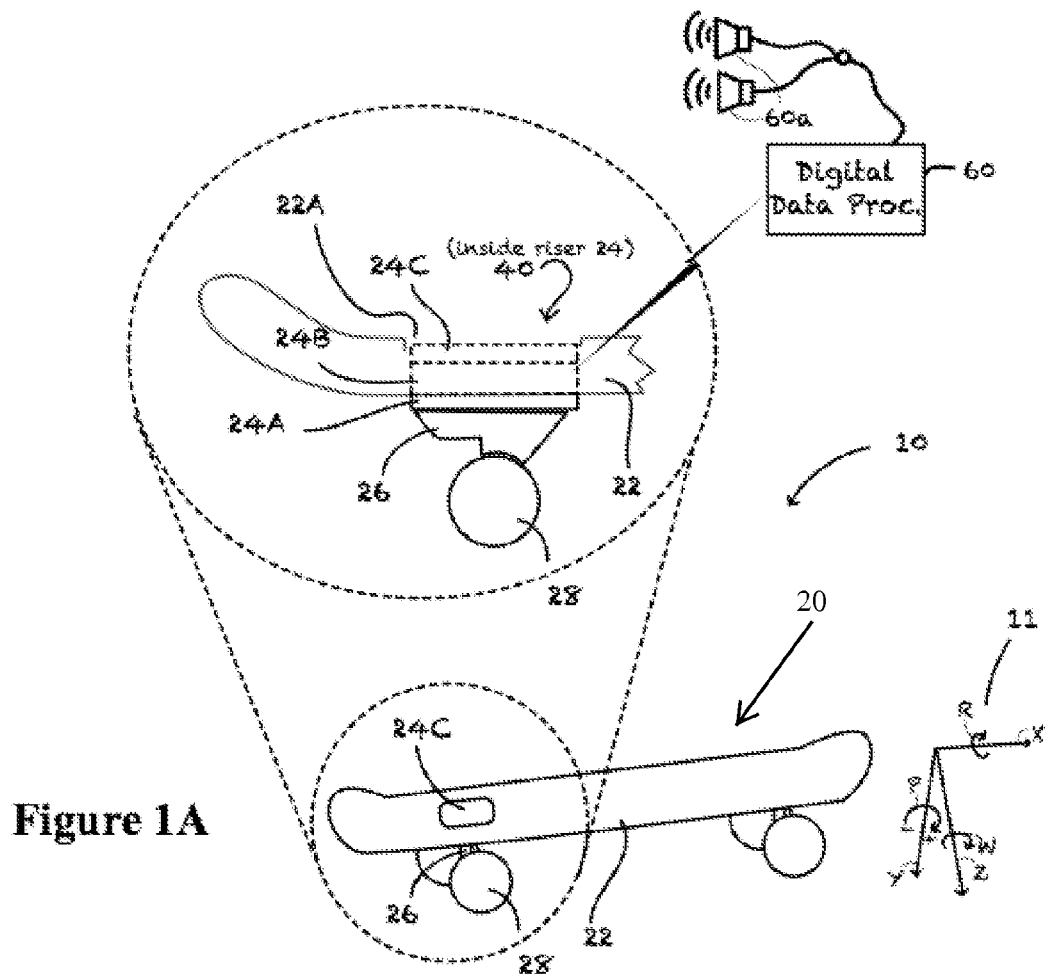

(60) Provisional application No. 61/370,439, filed on Aug. 3, 2010, provisional application No. 61/371,161, filed on Aug. 5, 2010, provisional application No. 61/386,207, filed on Sep. 24, 2010, provisional application No. 61/514,752, filed on Aug. 3, 2011, provisional application No. 61/514,773, filed on Aug. 3, 2011.

(51) Int. Cl.
    *G06F 19/00*     (2011.01)
    *G01C 23/00*     (2006.01)
    *H04R 1/02*     (2006.01)
    *A63C 17/26*     (2006.01)
    *A63C 17/01*     (2006.01)

(52) U.S. Cl.
    CPC ......... *A63C 2203/18* (2013.01); *A63C 2203/24* (2013.01); *G06F 17/40* (2013.01); *G06F 19/00* (2013.01)

(56) References Cited

U.S. PATENT DOCUMENTS

| | | | | |
|---|---|---|---|---|
| 5,317,305 | A * | 5/1994 | Campman | 340/573.1 |
| 5,857,939 | A * | 1/1999 | Kaufman | 482/8 |
| 6,179,746 | B1 * | 1/2001 | Delman | 482/6 |
| 6,244,987 | B1 * | 6/2001 | Ohsuga et al. | 482/4 |
| 6,244,988 | B1 * | 6/2001 | Delman | 482/8 |
| 6,251,048 | B1 * | 6/2001 | Kaufman | 482/8 |
| 6,368,217 | B2 | 4/2002 | Kanno et al. | |
| 6,582,342 | B2 * | 6/2003 | Kaufman | 482/8 |
| 7,160,200 | B2 * | 1/2007 | Grober | 473/234 |
| 7,383,728 | B2 * | 6/2008 | Noble et al. | 73/379.01 |
| 7,670,263 | B2 * | 3/2010 | Ellis et al. | 482/8 |
| 7,739,076 | B1 | 6/2010 | Vock et al. | |
| 7,807,913 | B2 * | 10/2010 | Choi et al. | 84/600 |
| 7,905,815 | B2 * | 3/2011 | Ellis et al. | 482/8 |
| 7,927,253 | B2 * | 4/2011 | Vincent et al. | 482/9 |
| 8,033,959 | B2 * | 10/2011 | Oleson et al. | 482/9 |
| 8,221,290 | B2 * | 7/2012 | Vincent et al. | 482/8 |
| 8,241,184 | B2 * | 8/2012 | DiBenedetto et al. | 482/9 |
| 8,251,875 | B2 * | 8/2012 | Ellis et al. | 482/8 |
| 8,337,335 | B2 * | 12/2012 | Dugan | 473/409 |
| 8,430,770 | B2 * | 4/2013 | Dugan | 473/409 |
| 8,452,259 | B2 * | 5/2013 | Ellis et al. | 455/410 |
| 8,562,490 | B2 * | 10/2013 | Dibenedetto et al. | 482/9 |
| 8,579,767 | B2 * | 11/2013 | Ellis et al. | 482/8 |
| 8,652,009 | B2 * | 2/2014 | Ellis et al. | 482/8 |
| 8,652,010 | B2 * | 2/2014 | Ellis et al. | 482/8 |
| 8,694,136 | B2 * | 4/2014 | Ellis et al. | 700/91 |
| 8,715,139 | B2 * | 5/2014 | Dibenedetto | A63B 24/0062 434/247 |
| 8,725,276 | B2 * | 5/2014 | Ellis et al. | 700/91 |
| 8,740,752 | B2 * | 6/2014 | Ellis et al. | 482/8 |
| 8,795,137 | B2 * | 8/2014 | Ellis et al. | 482/8 |
| 8,808,102 | B2 * | 8/2014 | Dugan | 473/223 |
| 8,808,114 | B2 * | 8/2014 | Dugan | 473/409 |
| 8,858,453 | B2 * | 10/2014 | Asukai et al. | 600/500 |
| 8,894,548 | B2 * | 11/2014 | Ellis | A61B 5/1038 482/1 |
| 8,923,998 | B2 * | 12/2014 | Ellis et al. | 700/94 |
| 2001/0001303 | A1 * | 5/2001 | Ohsuga et al. | 482/5 |
| 2002/0028730 | A1 * | 3/2002 | Kaufman | 482/8 |
| 2003/0171189 | A1 * | 9/2003 | Kaufman | 482/8 |
| 2003/0186785 | A1 | 10/2003 | Desberg et al. | |
| 2003/0215777 | A1 * | 11/2003 | Loveless | 434/247 |
| 2003/0216228 | A1 * | 11/2003 | Rast | 482/84 |
| 2004/0102931 | A1 * | 5/2004 | Ellis et al. | 702/188 |
| 2004/0215958 | A1 * | 10/2004 | Ellis et al. | 713/155 |
| 2006/0063600 | A1 * | 3/2006 | Grober | 473/224 |
| 2006/0170562 | A1 * | 8/2006 | Choi et al. | 340/573.1 |
| 2006/0227007 | A1 | 10/2006 | Landrieve | |
| 2007/0015611 | A1 * | 1/2007 | Noble et al. | 473/450 |
| 2007/0060446 | A1 * | 3/2007 | Asukai et al. | 482/8 |
| 2007/0111811 | A1 * | 5/2007 | Grober | 473/131 |
| 2007/0118328 | A1 | 5/2007 | Vock et al. | |
| 2007/0184940 | A1 | 8/2007 | Tomes | |
| 2007/0235957 | A1 | 10/2007 | Nenov et al. | |
| 2007/0260483 | A1 | 11/2007 | Nurmela et al. | |
| 2007/0282564 | A1 | 12/2007 | Sprague et al. | |
| 2008/0085778 | A1 * | 4/2008 | Dugan | 473/223 |
| 2009/0048070 | A1 * | 2/2009 | Vincent et al. | 482/8 |
| 2009/0098980 | A1 | 4/2009 | Waters | |
| 2009/0119030 | A1 | 5/2009 | Fang et al. | |
| 2009/0233770 | A1 * | 9/2009 | Vincent et al. | 482/8 |
| 2009/0237564 | A1 | 9/2009 | Kikinis et al. | |
| 2009/0303204 | A1 | 12/2009 | Nasiri et al. | |
| 2009/0305206 | A1 | 12/2009 | Lipetz | |
| 2010/0056340 | A1 * | 3/2010 | Ellis et al. | 482/4 |
| 2010/0056876 | A1 * | 3/2010 | Ellis et al. | 600/300 |
| 2010/0062740 | A1 * | 3/2010 | Ellis et al. | 455/351 |
| 2010/0130298 | A1 * | 5/2010 | Dugan et al. | 473/223 |
| 2010/0216551 | A1 | 8/2010 | Dwyer et al. | |
| 2010/0292050 | A1 * | 11/2010 | DiBenedetto et al. | 482/9 |
| 2011/0010129 | A1 | 1/2011 | Kirby | |
| 2011/0060550 | A1 | 3/2011 | Vock et al. | |
| 2011/0124387 | A1 | 5/2011 | Sauerbrei et al. | |
| 2012/0028762 | A1 * | 2/2012 | Oleson et al. | 482/9 |
| 2012/0116714 | A1 * | 5/2012 | Rogel et al. | 702/150 |
| 2012/0274469 | A1 * | 11/2012 | Oleson et al. | 340/573.1 |
| 2013/0083941 | A1 * | 4/2013 | Rogel | H04R 1/02 381/86 |
| 2013/0085713 | A1 * | 4/2013 | Rogel et al. | 702/141 |
| 2013/0095940 | A1 * | 4/2013 | Dugan | 473/222 |
| 2013/0184841 | A1 * | 7/2013 | Ellis et al. | 700/91 |
| 2013/0184843 | A1 * | 7/2013 | Ellis et al. | 700/94 |
| 2013/0190906 | A1 * | 7/2013 | Ellis et al. | 700/91 |
| 2013/0190907 | A1 * | 7/2013 | Ellis et al. | 700/91 |
| 2013/0190908 | A1 * | 7/2013 | Ellis et al. | 700/91 |
| 2013/0225335 | A1 * | 8/2013 | Dugan | 473/422 |
| 2013/0226321 | A1 * | 8/2013 | Ellis et al. | 700/91 |
| 2013/0249709 | A1 * | 9/2013 | Ellis et al. | 340/870.07 |
| 2014/0056437 | A1 * | 2/2014 | DiBenedetto et al. | 381/77 |
| 2014/0088739 | A1 * | 3/2014 | Ellis et al. | 700/91 |
| 2014/0094941 | A1 * | 4/2014 | Ellis et al. | 700/91 |
| 2014/0097967 | A1 * | 4/2014 | Ellis et al. | 340/870.07 |
| 2014/0100677 | A1 * | 4/2014 | Ellis et al. | 700/91 |
| 2014/0270236 | A1 * | 9/2014 | Dibenedetto et al. | 381/77 |
| 2014/0335965 | A1 * | 11/2014 | Dugan | 473/222 |
| 2014/0335978 | A1 * | 11/2014 | Dugan | 473/464 |

OTHER PUBLICATIONS

[No Author] Components. Solderin' Skaters. Retrieved Nov. 17, 2011 from solderinskaters.net/components.jpg. Photograph (1 Page).

[No Author] Description. Solderin' Skaters. Retrieved Nov. 17, 2011 from solderinskaters.net/description.jpg. Photograph (1 Page).

[No Author] Live Demo of the tilt'n'roll application. Solderin' Skaters Blog. Nokia PUSH. Retrieved Nov. 17, 2011 from blogs.nokia.com/pushn900/category/solderin-skaters/. Oct. 5, 2010 (6 Pages).

[No Author] Nokia+Burton=Push Snowboarding. Be Sportier: Men's Sportwear & Men's Gear. Retrieved Nov. 17, 2011 from besportier.com/archives/nokia-burton-push-snowboarding.html. Apr. 7, 2011 (3 Pages).

[No Author] Nokia PUSH N900 Solderin' Skaters Session 3: Designing the board and the 'Tilt'n Roll' software. YouTube video (screen shot) dated Jan. 19, 2010. (2 Pages).

[No Author] Nokia PUSH N900 Solderin' Skaters Session 4: Completing the 'Tilt'n Roll' App and App and final board design. YouTube video (screen shot) dated Jan. 28, 2010. (2 Pages).

[No Author] Nokia PUSH N900 Solderin' Skaters Week 1: Introduction, brainstorming and planning. YouTube video (screen shot) dated Dec. 15, 2009. (2 Pages).

[No Author] Nokia PUSH N900 Solderin' Skaters Week 2: Practical testing stage. YouTube video (screen shot) dated Dec. 23, 2009. (2 Pages).

[No Author] PUSH Nokia N8 Project Submission Deadline Extended! Symbian Freak. Retrieved Nov. 17, 2011 from .symbian-freak.com/news/010/10/push_n8_submission_deadline_extended.html. Sep. 13, 2009. (4 Pages).

(56) References Cited

OTHER PUBLICATIONS

[No Author] Solderin' Skaters.Solderin' Skaters. Retrieved Nov. 17, 2011 from solderinskaters.net/solderinskaters-pressinfo.pdf. Press Release. (2 Pages).

[No Author] The Solderin' Skaters. YouTube video (screen shot) dated Sep. 10, 2010. (2 Pages).

[No Author] Solderin' Skaters: Using the Trick simulator and Live skating session with the Nokia N900. YouTube video (screen shot) dated May 1, 2010. (2 Pages).

[No Author] Tony back on the street. Retrieved Nov. 17, 2011. (3 Pages).

International Search Report and Written Opinion mailed Dec. 16, 2011 for Application No. PCT/US2011/46423 (11 Pages).

International Search Report and Written Opinion mailed Nov. 8, 2012 for Application No. PCT/US2012/49421 (18 Pages).

International Search Report and Written Opinion mailed Nov. 2, 2012 for Application No. PCT/US2012/49423 (13 Pages).

International Preliminary Report on Patentability mailed Feb. 27, 2014 for Application No. PCT/US2011/46423 (8 Pages).

\* cited by examiner

DEVICES, SYSTEMS, AND METHODS FOR GAMES, SPORTS, ENTERTAINMENT AND OTHER ACTIVITIES OF ENGAGEMENT

REFERENCE TO RELATED APPLICATIONS

This application claims the benefit of filing of U.S. Provisional Patent Application No. 61/514,752, filed Aug. 3, 2011, entitled "Devices, Systems, and Methods for Games, Sports, Entertainment and Other Activities of Engagement,"

claims the benefit of filing of U.S. Provisional Application No. 61/514,773, filed Aug. 3, 2011, entitled "Signature-Based Trick Determination Systems and Methods for Skateboarding and Other Activities of Motion,"

is a continuation-in-part of and claims the benefit of filing of PCT Application No. PCT/US11/46423, filed Aug. 3, 2011, and published as WO 2012/018914 on Feb. 9, 2012, entitled "Digital Data Processing Systems And Methods For Skateboarding and Other Social Sporting Activities," which, itself claims the benefit of filing of commonly assigned U.S. Provisional Patent Application Ser. No. 61/370,439, filed Aug. 3, 2010, U.S. Provisional Patent Application Ser. No. 61/371,161, filed Aug. 5, 2010, and U.S. Provisional Patent Application Ser. No. 61/386,207, filed Sep. 24, 2010, all entitled "DIGITAL DATA PROCESSING SYSTEMS AND METHODS FOR SKATEBOARDING AND OTHER SOCIAL SPORTING ACTIVITIES,"

is a continuation of and claims the benefit of filing of pending abandoned U.S. application Ser. No. 13/197,429, filed Aug. 3, 2011, and published as US-2012-0116714-A1 on May 10, 2012, entitled "Digital Data Processing Systems and Methods for Skateboarding and Other Social Sporting Activities," which, itself, claims the benefit of filing of commonly assigned U.S. Provisional Patent Application Ser. No. 61/370,439, filed Aug. 3, 2010, U.S. Provisional Patent Application Ser. No. 61/371,161, filed Aug. 5, 2010, and U.S. Provisional Patent Application Ser. No. 61/386,207, filed Sep. 24, 2010, all entitled "DIGITAL DATA PROCESSING SYSTEMS AND METHODS FOR SKATEBOARDING AND OTHER SOCIAL SPORTING ACTIVITIES."

The teachings of all of the foregoing applications and publications are incorporated by reference herein.

This application is related to co-pending, commonly assigned U.S. patent application Ser. No. 13/565,971, and PCT Application Serial No. PCT/US2012/049423, both filed this same day herewith, and both entitled "Signature-Based Trick Determination Systems And Methods For Skateboarding And Other Activities Of Motion," the teachings of both of which are incorporated herein by reference.

BACKGROUND OF THE INVENTION

The invention relates to systems and methods for games, sports, entertainment and other activities of engagement. It has application in entertainment, sports and in training, among other things. Thus, by way of non-limiting example, it has application in training skateboarders in safety, as well as in providing games through which they may gain exercise and entertainment.

Games and sports, as well as the training that make them possible, are among the gainful diversions at which persons, communities and nations at peace engage. Technological advances in game, sports and training equipment help stave off contempt of the familiar, while, at the same time, feeding the drive for perfection.

Technology, however, usually follows and rarely leads. Most modern sports equipment, for example, does less to open new avenues of competition as opposed to perfection of old ones. Even video games, which post-date the vast majority of known games and sports, often merely seek to simulate them in virtual spaces.

An object of the invention is to provided devices, systems and methods for games, sports, entertainment and other activities of engagement.

A related object of the invention is to provide such devices, systems and methods as open new avenues for such activities, as well as improving existing games, sports and other activities.

A further related object of the invention is to provide such improved devices, systems and methods as have application in skateboarding.

Still further related objects of the invention provide such improved devices, systems and methods as have application in surfboarding, snowboarding, skiing, rollerblading and other activities.

SUMMARY OF THE INVENTION

The foregoing are among the objects attained by the invention, which provides in some aspects devices, systems, and methods for generating audio for a user/operator and for providing audio feedback in response to user/operation actions in response. Such devices, systems and methods have application, by way of non-limiting example, to games, sports, entertainment, training and other endeavors (including, by way of example, skateboarding, surfboarding, snowboarding, skiing, rollerblading, and training therefor) as well as to training therefor. Devices, systems and methods according to the invention are advantageous, among other reasons, because they allow users to pursue and/or obtain audio-prompted goals through real-world physical action.

A system according to one such aspect of the invention comprises (i) a sensing device that is attached (or otherwise coupled) to a skateboard and that measures a physical characteristic of it and/or of its environment, (ii) an audio output device, and (iii) a digital data processor that is communicatively coupled to the audio output device and the sensor. The digital data processor drives the audio output device to effect one or more selected sounds (e.g., to prompt the user to perform a selected action). The digital data processor, further, and monitors the sensing device to identify user actions in response to those sounds and drives the audio output device to effect still further sounds based on those actions.

Related aspects of the invention provide systems, e.g., as described above, in which the digital data processor drives the audio output to effect sounds as a function of scripts, guidelines, programming or other rules (collectively, "rules") and/or data that (a) define the game, sport, entertainment activity, training exercise or other endeavor for which the skateboard is being used, and/or (b) a virtual sound space in which that endeavor is exercised—i.e., an auditory space, preferably, of three-dimensions, in which everything from other players, to characters, to obstacles, to scenery, to the actor representing the skateboard operator, his/her game status, the skateboard movements (or other interactions) with the foregoing are represented to the operator by sounds, yet, where, the user effects those movements and interactions by moving and/or performing tricks (or feats) with that skateboard in the real and physical space surrounding him/her.

Further related aspects of the invention provide systems, e.g., as described above, in which the digital data processor drives the audio output to effect sounds defining at least a portion of the virtual sound space in a vicinity of an actor represented by the skateboard and/or its operator. Still further related aspects of the invention provide systems, e.g., as described above, in which the digital data processor drives the audio output to effect sounds reflecting the skateboard operator's (and/or the skateboard's) interaction with that virtual sound space.

Other aspects of the invention provide systems, e.g., as described above, in which the digital data processor drives the audio output device to effect a voice, e.g., commanding the skateboard user to take a particular action—for example, to skate in a designated direction, to perform a specified trick, and so forth). Based on the user's response (e.g., determined by monitoring the sensing device), the digital data processor can drive the audio output device to effect sounds of approval/disapproval or degrees thereof (e.g., applause, boos, ratings, etc.) and/or to effect a voice commanding further action.

Further related aspects of the invention provide systems, e.g., as described above, in which the digital data processor drives the audio output device to simulate sounds of an object near or far from the user and/or moving relative thereto. Based on the user's response (e.g., determined by monitoring the sensing device), the digital data processor determines whether the user moved in a prescribed manner relative to the simulated object—for example, increased/decreased a distance to the object, reached a spot representing a location of the object, overtook the object, avoided the object, and so forth. Alternatively, or in addition, the digital data processor can determine whether the user performed a trick or other action on the skateboard that is interpreted—e.g., according to rules of a game, sport or other pursuit—as touching, capturing, shooting, freeing, or taking some other action with respect to the simulated object.

Still further related aspects of the invention provide systems, e.g., as described above, in which the digital data processor drives the audio output device to simulate sounds of an object that is imaginary, e.g., a dragon, a shooter or a virtual competitor. In other such aspects, it drives the audio output device to simulate sounds of an object whose position and/or actions are based on a real-world object, e.g., another skateboarder (who, too, is equipped with a system according to such aspects of the invention), another person (whether or not on a skateboard), or any other object (e.g., a moving vehicle, an ocean wave, and so forth).

Further aspects of the invention provide systems, e.g., as described above, in which (i) sensing device is coupled to the operator and particularly, for example, his/her shoes, etc., instead or in addition to being coupled to the skateboard, and/or (ii) the data processor is coupled to the skateboard and/or operator, for example, in the form of an add-on or integral module (e.g., in the case of the skateboard) or a clip-on, wearable, pocketable, or carry-along (e.g., in the case of a operator).

In other aspects, the invention provides systems as described above in which the sensing device is attached or otherwise coupled to a surfboard, rollerblade boot, ski, ski boot, surfboard or other object (and/or the operator thereof) in lieu of a skateboard (and/or operator thereof)—thus, making possible, engaging in other games, sports, entertainment, training and other endeavors.

Further aspects of the invention provide systems, e.g., as described above, in which the sensing device is gyroscopic and/or otherwise measures rotation of the skateboard and/or its operator. This can include, for example, gyroscopic sensors that measure such rotation, preferably along at least two—and, still more preferably, along at least three—of x-, y- and z-axes. According to other aspects of the invention, other sensors suitable for detecting rotational and/or other physical characteristics of the skateboard (and/or operator) are used instead or in addition to gyroscopic sensors. These include, by way of non-limiting example, accelerometers, magnetometers, global positioning sensors, strain sensors, or other sensor(s) capable of indicating speed, acceleration, jerk, yaw, pitch, roll, or other physical characteristics of the skateboard, its user and/or the its environment.

Still further related aspects of the invention provide systems, e.g., as described above, in which the data processor is disposed remotely from the skateboard, yet, coupled for communications with it (and, more particularly, for example, the sensing devices). Such a "remote" data processor can be a dedicated device or it can be part a multifunction device, e.g., as in the case of a data processor that is embedded in a cell phone, personal digital assistant, or other mobile device (collectively, "mobile device"), that performs other functions, e.g., in addition to driving prompts to the audio output device and providing further audio feedback in response to user/operation actions in response to those prompts.

Further aspects of the invention provide systems, e.g., as described above, in which the sensing device communicates with such a remote data processor wirelessly, e.g., via BLUETOOTH, WIFI, cellular, infrared or other wireless or wired transmission medium, or otherwise. The data processor can optionally log and/or display measurements received from the sensor(s), e.g., in addition driving the audio output device based on those measurements. An advantage of such logging is, for example, that it makes possible validating what games, sports or other endeavor the operator effected on the skateboard (or other object) as well, for example, as the success of that endeavor.

Yet still other aspects of the invention provide systems, e.g., as described above, that includes two (or more) data processors, e.g., one that is coupled to the skateboard and/or operator, and one that is disposed remotely. The two (or more) data processors can be coupled for communications via wire and/or wirelessly. They may, moreover, share and/or divide up one or more of the tasks attributed to the "data processor" or "server" in this summary and elsewhere herein. Thus, for example, according to one such aspect of the invention, an "on-board" data processor that is coupled to the skateboard identifies tricks and other movements based on measurements made by the sensing device and routes those identifications to the remote digital data processor, for further processing by it to generate sound prompts (or sequences thereof) that are, in turn, routed back to the on-board data processor which drives the audio output device.

Further related aspects of the invention provide systems, for example, as described above, in which the server exchanges data between and/or among systems according to the invention, e.g., thereby, for example, enabling the playing of games among enthusiasts that are separated by time and/or space. Other related aspects of the invention provide such systems in which the server provides data regarding other real-world objects, e.g., other persons, moving vehicles, ocean waves, and so forth, to skateboard-based and/or other systems as described above, e.g., in order to enable their respective digital data processors to drive their respective audio output devices to simulate those objects.

Related aspects of the invention provide sensing devices as described above, e.g., for coupling to a skateboard, surfboard, rollerblade boot, or other object (and/or the operator thereof) and/or for communication with a data processor a described above.

Related aspects of the invention provide a data processor and/or mobile device incorporating same as described above.

Related aspects of the invention provide a server, laptop, desktop or other data processor as described above.

Related aspects of the invention provide methods of operating one or more of the a sensing devices, data processors, mobile device, laptops, desktops and/or server as described above.

Advantages of systems according to the invention are, among others, that they permit open new avenues for play, sport, training or engagement in other endeavors. For example, unlike prior art video game-based systems they do not rely on graphics or other visual effects. Not only does this increase the mobility of systems according to the invention, it decreases their cost, processing and equipment overhead. Moreover, it permits the experience the game, sport, training or other engagement at the same time that user participates in the real and physical world about him/her. In fact, by allowing the user to experience the game "in audio," he or she can direct the rest of his or her senses to, for example, skillfully manipulating the skateboard in the real world. This dual, simultaneous interactions with the virtual sound space and the real world can be beneficial not only to game and sports enthusiasts, but to others, as well. e.g., the vision-impaired, new employees and others who are training in the ways of their new place of employ, and so forth, all by way of non-limiting example.

BRIEF OF ILLUSTRATED EMBODIMENT

Figure 1B:
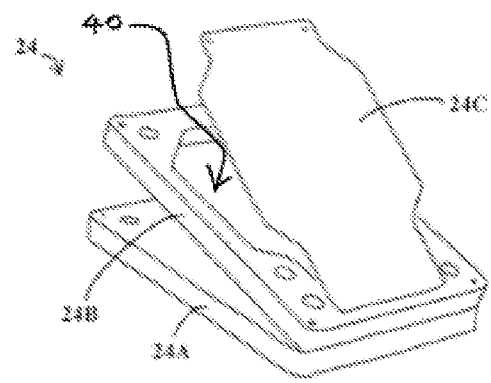
Figure 2A:
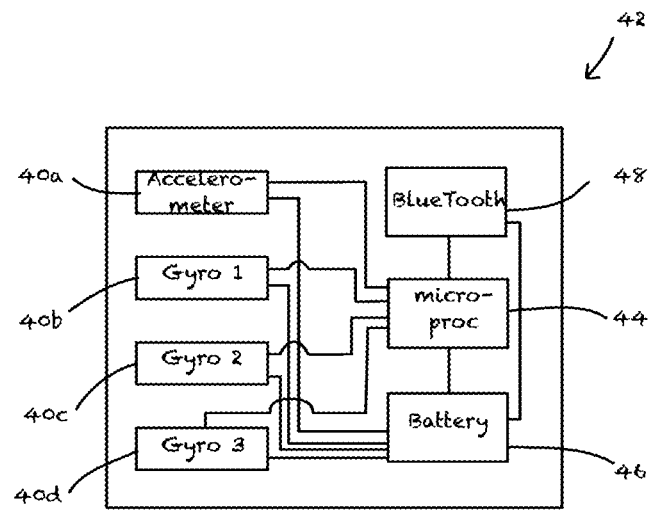
Figure 2B:
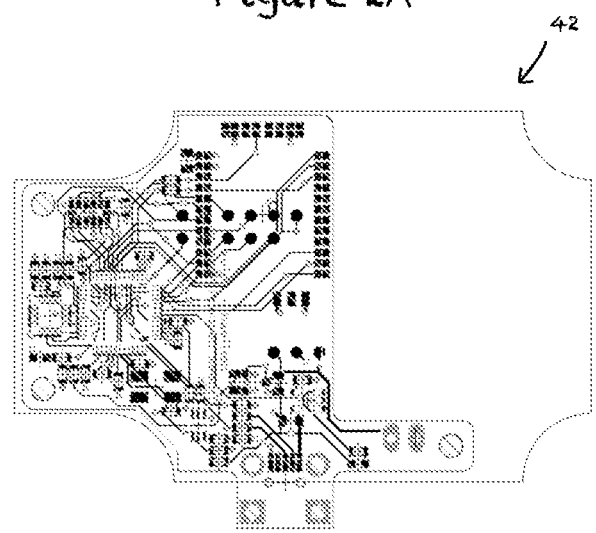
Figure 3:
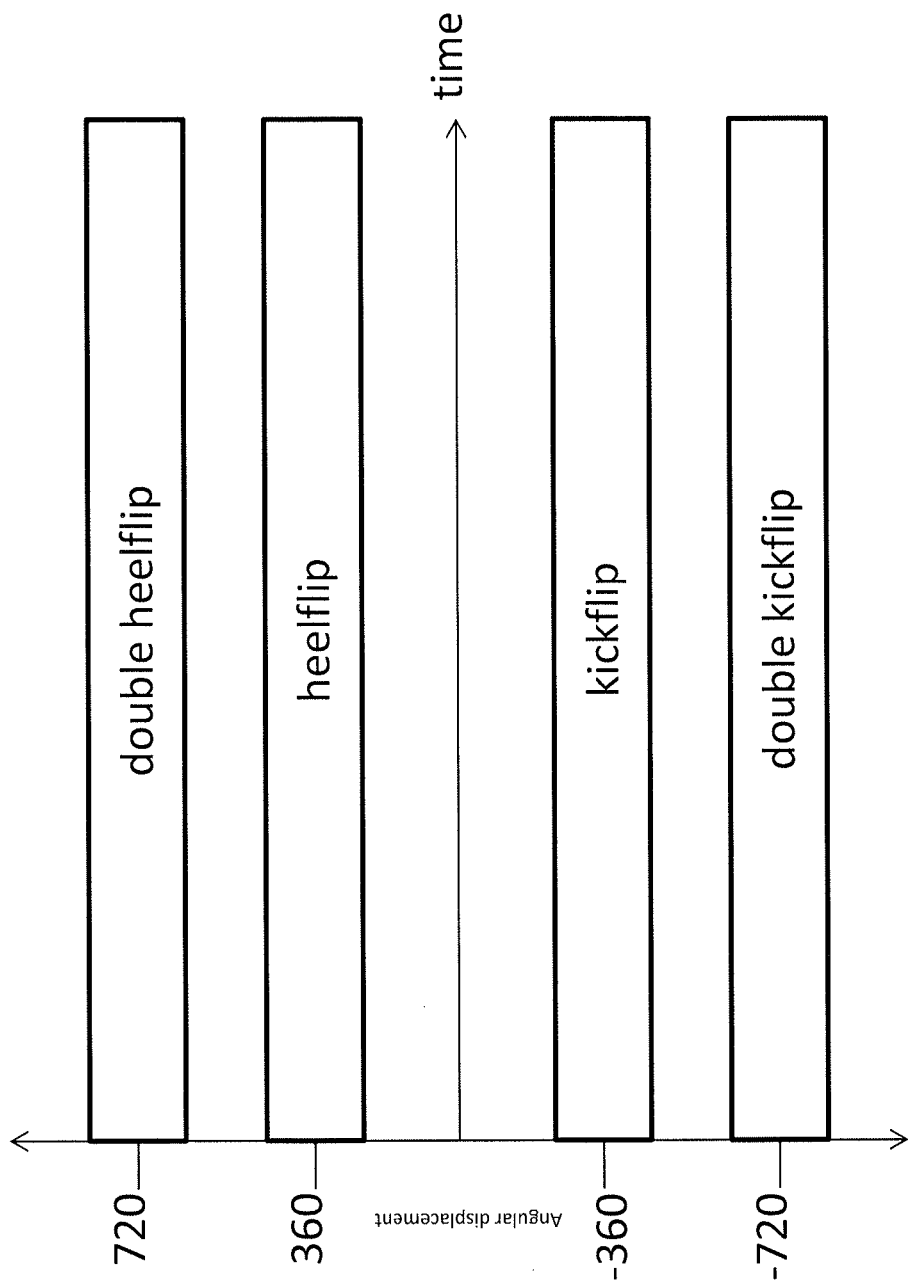
Figure 4:
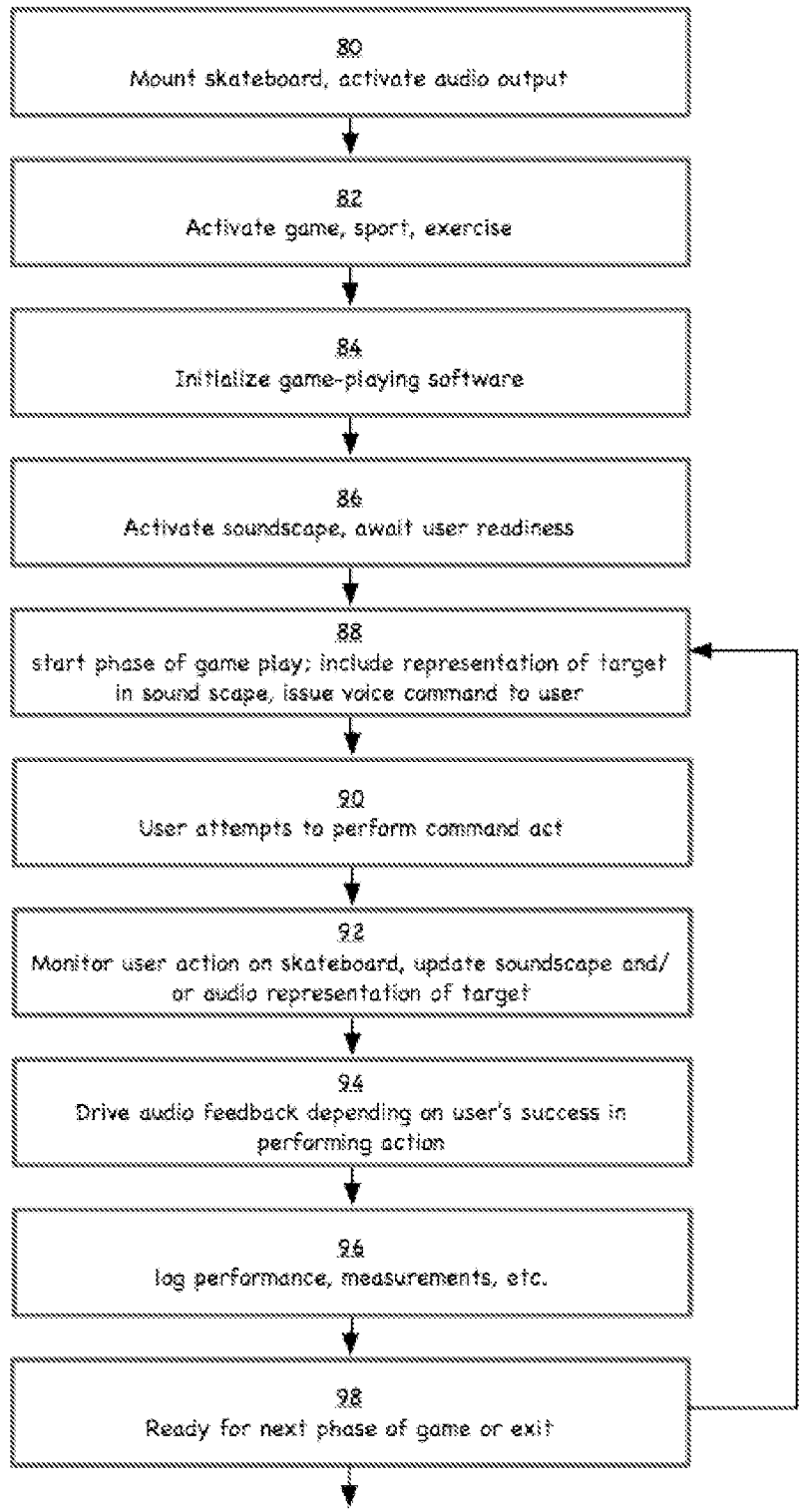

A more complete understanding of the invention may be attained by reference to the drawings, in which:

FIG. 1A-1B depict a system according to the invention for generating audio prompts to a skateboard user and for providing audio feedback in response to his/her actions in response to those prompts;

FIGS. 2A-2B schematically depicts a sensing device according to the invention for use in the system of FIG. 1;

FIG. 3 depicts an aspect of trick identification in a system according to the invention; and FIG. 4 is a flowchart depicting operation of a digital data processor according to one practice of the invention enabling an operator to use a skateboard and system to engage in a voice-prompted, one-person (or "single-player") game, sport, entertainment activity, training exercise or other endeavor in a virtual sound space.

DETAILED DESCRIPTION OF THE ILLUSTRATED EMBODIMENT

Systems according to the invention comprise hardware and/or software that generate audio for games, sports, entertainment, training and other endeavors and that provide audio feedback in response to the enthusiasts actions in response to those prompts. As noted above, such systems (as well as the underlying devices and methods) are advantageous, among other reasons, because they allow users to pursue and/or obtain audio-prompted goals through real-world physical action: without loss of generality, they are referred to herein as systems for "audio games," "physically interactive audio games," and so forth, as will be evident below.

For sake of convenience, and without loss of generality, such systems are described in connection with skateboarding in much of the discussion below, though, it will be appreciated that the invention can be used in connection other games, sports, entertainment, training and other endeavors (such as skateboarding, surfboarding, snowboarding, skiing, and rollerblading, among others).

Unlike the prior art, in which the technology merely tend to enhance known game, sport, entertainment, training and other experiences, devices, systems and methods according to the invention additionally open new avenues of play, e.g., by combining physical activity with virtual spaces—and, particularly, with auditory virtual spaces. Such devices, systems and methods make possible, for example, engagement in games, sports, entertainment, training and other endeavors in virtual sound spaces (or "virtual sound worlds")—e.g., auditory spaces defined by sound—preferably, in three-dimensions i.e., an auditory space, preferably, of three-dimensions, in which everything from other players, to characters, to obstacles, to scenery, to the actor representing the skateboard operator, his/her game status, the skateboard movements (or other interactions) with the foregoing are represented to the operator by sounds—yet, where, the user effects those movements and interactions by moving and/or performing tricks (or feats) with that skateboard in the real and physical space surrounding him/her.

In addition to enhancing and/or opening new avenues for play, sport and/or training by individual enthusiasts, devices, systems and methods according to the invention enhance competition between and among such enthusiasts—even those separated by time and space.

Architecture (FIG. 1A)

FIG. 1A depicts a system 10 according to one practice of the invention for physically interactive audio games. Other embodiments employing the teachings hereof and within the ken of those of ordinary skill in the art may be utilized for identifying other feats of motion of the user alone or in connection with other objects. Non-liming examples of other such objects (and feats of motion) include, inter alia, surfboards, snowboards, skis, and rollerblades, among others.

The illustrated system includes one or more sensing devices 40 (also referred to here as measurement devices) that are attached to a skateboard 20 and that are in communications coupling with one or more digital data processors, here, in this drawing, represented by digital data processor 60. The illustrated system further includes an audio output device, e.g., such as earphones 60a.

Sensing Devices

The sensing devices 40 measure position, motion and/or other physical characteristics of the skateboard 20 and/or its environment. Position measurements can include absolute or relative position (e.g., as determined in accord with GPS satellite signals or otherwise), linearly or in rotation—including, by way of non-limiting example, location, orientation and/or altitude. Referring to the annotated axes 11 shown on FIG. 1A, motion measurements can include linear motion and/or rotation motion, including, for example:

1) roll (denoted "R", in the drawing)—total angular displacement about the longest principle axis X of the skateboard given relative positioning of the sensors to the skateboard;
2) pitch P—total angular displacement about the second principle axis Y of the skateboard parallel to the ground when the skateboard is at rest on its wheels;
3) yaw ("W")—total angular displacement about the principle axis Z of the skateboard perpendicular to the ground when the skateboard is at rest on its wheels;
4) acceleration—acceleration detected along the longest axis X of the skateboard;

5) initial pitch—the sign of the pitch P detected nearest the start point of the data window. In the drawing, that sign is indicated by "+" and "−" signs adjacent ends of the curved arrow denoting the pitch P.

Other motion measurements can include speed, jerk, among others. Other characteristics of the skateboard can include orientation of the operator/user, weight of the operator/user and/or other forces and strains on the skateboard, temperature and windspeed, all by way of non-limiting example.

The sensing devices 40 can comprise conventional sensors of the type for measuring linear and/or rotations position and/or motion known in the art, as adapted in accord with the teachings hereof. Thus, for example, the devices 40 may comprise GPS sensors, accelerometers, gyroscopes, magnetometers, temperature sensors, strain sensors, optical sensors, acoustic sensors, RFID (radio frequency identification) and so forth embodied in microelectromechanical systems (MEMS) or otherwise, and all as adapted in accord with the teachings hereof. For example, in some embodiments, optical sensors are utilized alone—or, for example, with LED lasers or other light-emitting devices—to facilitate detecting when the skateboard 20 is engaged in a "grind." By way of further example, in some embodiments, an RFID receiver chip attached to the skateboard 20 can be used in conjunction with an RFID transmitter chip attached to the user's shoes (or elsewhere) to facilitate (i) identification and/or orientation of the user.

Placement

The sensing devices 40 can be coupled to any portion of the skateboard 20—though, in some embodiments, placement is dictated by several factors related to standard use cases: where on the board will the sensing devices experience the least damage, what is least intrusive to the skateboarding experience, and what is most aesthetically pleasing.

Significantly, placement is also dictated by location(s) that facilitate measurement by sensing devices 40 (e.g., accelerometers), e.g., as optimized for the particular motions upon which operators are likely to rely during engagement in games, sports, entertainment, training and other endeavors.

For example, in embodiments that support trick detection (e.g., that permit the skateboard operator to incorporate tricks into game play—such as, for example, the execution of an "ollie" to shoot game characters that are nearby in the virtual sound space established by the system) these are locations that are best interpreted by data processor 60 to identify tricks performed on a skateboard (and/or to otherwise provide for the meaningful generation of data pertaining to the skateboard). In this regard, placement can be made in accord with an analytic solution to the three coupled differential equations for rigid body motion known as Euler's equations. Precise placement in this regard is not critical, however, since the set of motions that constitute skateboard tricks is sufficiently limited to admit coarser methods of distinction (and, hence, allowing more weight to be given to the other placement factors).

By placing the sensing devices on the skateboard asymmetrically along its longest principle axis and approximately symmetrically along the remaining two principle axes one can sense the centrifugal acceleration in the rotating frame necessarily experienced when the skateboard rotates about a nonprinciple axis during a trick. This hinges on how limited the class of rigid body motions that constitute tricks is: any trick that does not rotate solely about a principle axis necessarily has largest angular velocity in roll and registers non-zero angular velocity about all three principle axes for the duration of a trick. In the standard language of skateboarding the first of these characterizations is tantamount to saying that if two tricks that rotate about a single principle axis are combined, one of them will be a kickflip or a heelflip.

This partially symmetric placement of sensors can be used to detect centrifugal acceleration of the skateboard 20 (or other object) along its longest principle axis, which in turn is useful in developing a myriad of coarse yet unambiguous classifications of rigid body motion. The outlined sensor placement criteria has broad application in many fields outside of skateboarding. Indeed, any activity of motion involving a rigid body that has a distinctly long principle axis would benefit from this scheme in tracking and classifying rigid body motion.

Riser Pad (FIG. 1B)

Referring to FIG. 1B, the sensing devices 40 can be embedded, mounted or otherwise fixed to the trucks 26, which connect wheels 28 to deck 22. Alternatively, the devices 40 can be affixed to a surface of the deck 22 or elsewhere on the skateboard.

Regardless, the sensing devices are preferably mounted to the skateboard 20 in a manner that achieves the desired placement while, at the same time, (i) protecting the devices 40 from damage as the skateboard is stepped upon, grinded and/or slammed during use (e.g., jumped upon by the user, grinded against stair rails, slammed against curbs, and so forth), (ii) permitting access to batteries, sensors and associated logic of the sensing devices 40, (iii) permitting transmission of wireless signals to/from the sensing devices, e.g., without requiring signal penetration through the truck 26, which is typically metal, and/or (iv) permitting recharging of batteries for the devices 40, uploading of data and/or control software, and/or downloading of data.

A riser pad 24 that achieves the foregoing is illustrated in FIG. 1B. This pad 24, which is generally of a "clamshell" design, includes a base portion 24A, a body portion 24B, and a cover 24C. Those portions may be hinged to one another, as shown in the drawing, though this is not the case of all embodiments. And, while the cover 24C is preferably removable from the other portions 24A, 24B, those other portions may, indeed, be formed as one.

In the illustrated embodiment, the pad 24 is mounted in a cavity 22A of the deck 22 such that the cover 24C is accessible from the top of the deck (i.e., the side opposite the deck from the truck 26 and wheels 28) and such that the base 24A is accessible—and, preferably, stands proud from—the bottom of the deck 22. The latter permits, in some embodiments, mounting of the truck 26 to the base 24A and, in some embodiments, exposes a port (not shown here), e.g., a charging port and/or data port, for access by the operator when the board 20 is not in use.

Consistent with the discussion above, the pad 24 and, particularly, the body portion 24B thereof are disposed within deck 22 such that sensing devices 40 mounted within the pad 24 are disposed asymmetrically along the longest principle axis X of the skateboard, while being approximately symmetrically disposed along the remaining two principle axes Y, and Z, as shown. Though shown in an open configuration in the drawing, during normal use of the skateboard 20, the body of spacer 24 is disposed in recess 22A and is closed.

Portions 24A, 24B may be formed of metal, plastic, wood, carbon fiber or other material of suitable durability, e.g., for permanent or semipermanent affixation in deck 22 and for mounting of truck 26, as shown if FIG. 1A. Cover 24C is preferably formed of plastic, wood or other material sufficiently durable to withstand pounding, rubbing or other contact by the operator, yet, which does not interfere with wireless communications, e.g., to/from sensing devices 40 disposed within the pad 24. The various portions 24A-24C preferably includes seals, e.g., O-rings, or the like, that prevent water, dirt and other contaminants from entering the body and, thereby, fouling sensing devices 40 therein.

Multiple Sensing Devices

In some embodiments, more than one array of sensing devices 40 are be coupled to the skateboard to allow for additional data to be generated regarding the characteristic(s) of interest. For example, a skateboard 20 can have sensing devices, e.g., in spacers 24 that reside above the trucks of both the front and back wheels. In fact, in some embodiments, one or more of those sensing devices 40 is disposed on the user/operator of the skateboard, e.g., on a shoe, boot, sock, pant leg, belt, backpack, and so forth, in order to provide further data for identifying tricks performed on a skateboard and/or for otherwise generating, transmitting, and analyzing data pertaining to motion of the skateboard.

Digital Data Processor 60

The sensing devices 40 communicate collected measurements to one or more digital data processors—here, depicted as digital data processor 60—for (a) analysis in view of scripts, guidelines, programming or other rules (collectively, "rules") and/or data that define (i) the game, sport, entertainment activity, training exercise or other endeavor for which the skateboard 20 is being used, and/or (ii) the virtual sound space in which that endeavor is exercised, and (b) driving the audio output device 60a to effect sounds embodying at least a portion that virtual sound space (e.g., in a vicinity of the actor represented by the skateboard 20 and/or its operator) and/or the skateboard operator's interaction with that virtual sound space, e.g., as he or she effects moves and/or performs tricks (or feats) with the skateboard in the real and physical space surrounding him/her. In addition, the digital data processor can collect those measurements for logging, display and/or retransmission to other devices.

The data processor(s) can comprise a dedicated device, such as a dedicated microprocessor (or "controller") that is embedded with the sensing devices 40, e.g., on the skateboard 20, and/or that is housed separately from the sensing devices albeit coupled for medium, or otherwise. An example of the former is microprocessor 44 of Figures A and 2B. An example of the latter is the digital data processor 60 shown in FIG. 1 FIGS. 1A and 1B and discussed, e.g., in the section below entitled "Digital Data Processor."

Alternatively, or in addition, the data processor(s) 60 can be part a multifunction device, e.g., as in the case of a data processor that is embedded in a cell phone, personal digital assistant, or other mobile device (collectively, "mobile device") and that is in communications coupling (again, for example, via BLUETOOTH, WIFI, cellular, infrared, or other wireless or wired transmission medium, or otherwise) with the sensing devices 40 and/or another data processor (e.g., an embedded microprocessor) that is itself in communications coupling with those devices 40.

Sensing Device—Packaging (FIGS. 2A and 2B)

As noted above in connection with FIGS. 1A and 1B, the sensing devices 40 can comprise conventional sensors of the type known in the art for measuring position, motion and/or other physical characteristics of the skateboard 20 and/or its environment, as adapted in accord with the teachings hereof. Thus, for example, the devices 40 may comprise GPS sensors, accelerometers, gyroscopes, magnetometers, temperature sensors, strain sensors, and so forth, embodied in microelectromechanical systems (MEMS) or otherwise, and all as adapted in accord with the teachings hereof.

Referring to FIG. 2A, the sensing devices 40 of the illustrated embodiment comprise linear accelerometer sensor 40a and rotational sensors 40b-40d for measuring, respectively, acceleration along the longest axis X of the skateboard 20; roll (angular displacement about axis X), pitch (angular displacement about axis Y) and yaw (angular displacement about axis Z). As noted above, other embodiments may use other sensors, e.g., GPS sensors, magnetometers, temperature sensors, strain sensors, instead or in addition.

Illustrated sensing devices 40 may form part of an inertial measurement unit or otherwise, and they may be fabricated embodied in microelectromechanical systems (MEMS) or otherwise. In one embodiment, the rotational sensors 40b-40d are embodied in an STMicroelectronics L3G4000D three-axis angular rate sensor, while sensor 40a is embodied in an Analog Devices ADXL345 three-axis accelerometer. These, however, are design choices, from which others skilled in the art may vary in accord with the teachings hereof.

Packaged with the sensors 40a-40d of the illustrated embodiment are microprocessor 44, battery 46, and wireless communication module 48. Together with an appropriate substrate and supporting circuitry, these components form a printed circuit board (PCB) 42 that, in the illustrated embodiment, has a form factor of the type as shown in FIG. 2B. Of course, other embodiments may package these components in other ways—e.g., on PCBs of other configurations, on chipsets, in separate PCBs, and otherwise).

While not shown in the illustrated embodiment, the sensing devices can additionally include a pressure sensor (based on piezo-electric or otherwise). This can be housed on PCB 42, though, more typically, it is mounted directly to deck 22 in order to detect when there is a user on the skateboard 20, when the user is landing on the board (e.g., after a jump), when the user and board are both in free-flight and/or when the user falls off the board. Output from the pressure sensor can be used in connection with trick determination, e.g., along the lines discussed below and/or it can be reported (directly or by way of microprocessor 44) to digital data processor 60 as another "measured characteristic" of the board 20.

The device 42 can also incorporate the audio output module 60a discussed above in connection with FIGS. 1A and 1B.

Battery

Battery (or other power source) 48 provides power for operation of unit 42 and/or the constituent elements thereof. This is a conventional battery (or other power source) of the type known in the art for household or light industrial use, though other batteries and/or power sources may be used as well or in addition—all as adapted in accord with the teachings hereof. Suitable batteries include, for example, alkaline, nickel-metal hydride, nickel-cadmium, lithium, carbon zinc, and so forth. Preferably battery 48 is rechargeable and/or removable (e.g., via opening of riser cover 24c).

In the illustrated embodiment, battery 48 may be recharged (and its charge, for example, checked) via application of power to a USB port on unit 42, access to which may be gained via the base 24a or cover 24c of the riser 24. (That access may be covered, e.g., by a removable plug or otherwise to prevent contamination). In other embodiments, recharging may be provided for via a standard power adapter port, via inductive charging or otherwise.

Communication Module 46 Enables the Transfer of Software

Communication module 46 enables the transfer of software (e.g., for purposes of reprogramming the unit 42), control parameter and/or data between the unit 42 (and, particularly, for example, the sensors 40a-40d and/or microprocessor 44) and external devices, e.g., digital data processor 60. The module 46 can support wired transfers, e.g., via the aforementioned USB port or otherwise.

In preferred embodiments, it supports wireless transmissions, instead or in addition. This can include BLUETOOTH, WIFI, cellular, infrared or other wireless protocols.

Module 46 can be constructed and operated in the conventional manner known in the art suitable for supporting the aforesaid and other wired and wireless protocols—as adapted in accord with the teachings hereof.

Software of the type suitable for execution by microprocessor 44 to effect operation of module 46 of the illustrated embodiment is provided below. It will be appreciated that this represents but one technique for configuring the microprocessor 44 to support such operation and that other techniques so configuring the microprocessor are within the scope of the invention.

```python
# IMUcommBT.py

# Communicates with IMU through Bluetooth RFCOMM, logs data to files,
# Parses comma-separated, new-line/carriage-return divided lines of raw IMU
        sensor data
# has very basic error detection and alignment and circular buffering
import bluetooth
import time
import string
import numpy as np
def get_user_selection_of_BT_address( ):
    print "Searching for discoverable Bluetooth devices..."
    nearby_devices = bluetooth.discover_devices( )
    if nearby_devices == [ ]:
        print "Found no discoverable Bluetooth devices!"
        return None
    print "(Number) Name; Address"
    for n in range(len(nearby_devices)):
        print '(' + str(n) + '.) ' + \
              bluetooth.lookup_name(nearby_devices[n]) + '; ' + \
              nearby_devices[n]
    print " "
    def get_user_number_input(number_of_devices, selection = [ ]):
        if selection != [ ]:
            print '\'' + str(selection) + '\'' + ' is an invalid selection.'
        device_number = raw_input('Connect to (enter number): ')
        if int(device_number) in range(number_of_devices):
            return device_number
        else:
            get_user_number_input(number_of_devices, device_number)
    device_number = get_user_selection(len(nearby_devices))
    return nearby_devices[device_number]
# connect to IMU and return IMU Bluetooth socket
def getIMUsocket(address = '00:06:66:42:21:85'):
    sock = bluetooth.BluetoothSocket(bluetooth.RFCOMM)
    #alt_address = raw_input('Enter imu\'s Address (Default: ' + address +
            '):')
    #if alt_address != '':
    #    address = alt_address
    #nearby_devices = bluetooth.discover_devices( )
    #if address in nearby_devices:
        # print 'Connecting to ' + bluetooth.lookup_name(address) + "..."
    sock.connect((address, 1))
    #sock.setblocking(True)
    return sock
    #else:
    #    print "Could not connect to device with address " + address + "."
    #    return None
# returns Bluetooth buffer's raw data
def getPacket(socket):
    return socket.recv(1024)
# parses new sensor data into co-temporal sets
def parseIMUdata(rawdata):
    max_lines = 40
    bufList = \
        string.replace(string.replace(rawdata,'AN:',''),'!ANG:','').split
            ('\r\n')
    line = np.zeros((max_lines,7)) # elements in a complete line => 7
    num_lines = len(bufList)
    if rawdata[−1] != '\r\n':
        num_lines = num_lines − 1
    for i in range(num_lines):
        tmpLine = bufList[1].split(',')
        try:
            line[i,0] = int(tmpLine[3])
            line[i,1] = int(tmpLine[4])
            line[i,2] = int(tmpLine[5])
            line[i,3] = int(tmpLine[6])
            line[i,4] = int(tmpLine[7])
            line[i,5] = int(tmpLine[8])
            line[i,6] = int(tmpLine[9])
```

```
            except:
                line[i,0] = 0
        return [num_lines, line]
def parse(rawdata):
max_lines = 256
bufList = rawdata.split('\r\n')
line = np.zeros((max_lines,7))
num_lines = len(bufList)
for i in range(num_lines):
try:
data_array = np.fromstring(bufList[i], dtype=np.uint8)
#data_array = bytestring(bufList[i])
line[i,0] = 2**32*data_array[0] + 2**16*data_array[1] +
             2**8*data_array[2] + data_array[3]
line[i,1] = 2**8*data_array[4] + data_array[5]
line[i,2] = 2**8*data_array[6] + data_array[7]
line[i,3] = 2**8*data_array[8] + data_array[9]
line[i,4] = (2**8*data_array[10] + data_array[11]) - 2**12
line[i,5] = (2**8*data_array[12] + data_array[13]) - 2**12
line[i,6] = (2**8*data_array[14] + data_array[15]) - 2**12
except:
line[i,0] = 0
return [num_lines, line]
def parse(rawdata):
    bufList = rawdata.split('\r\n\r\n')
    num_lines = len(bufList)
    line = np.zeros((num_lines,7), np.int32)
    for i in range(num_lines):
        try:
            if (len(bufList[i])==16):
                data_array = np.fromstring(bufList[i], dtype=np.uint8)
                # timestamp
                line[i,0] = 2**32*data_array[0] + 2**16*data_array[1] +
                2**8*data_array[2] + data_array[3]
                # gyroscope data
                line[i,1] = 2**8*data_array[4] + data_array[5]
                line[i,2] = 2**8*data_array[6] + data_array[7]
                line[i,3] = 2**8*data_array[8] + data_array[9]
                # accelerometer data
                line[i,4] = (2**8*data_array[10] + data_array[11]) - 2**12
                line[i,5] = (2**8*data_array[12] + data_array[13]) - 2**12
                line[i,6] = (2**8*data_array[14] + data_array[15]) - 2**12
            else:
                line[i,0] = -1
        except:
            line[i,0] = -1
    return [num_lines, line]
# Open and return IMU log file object
def openIMUlogfile(filepath = './/' + time.strftime('%Y%m%dT%H%M%S')+ 'i-
    mu.txt'):
    alt_filepath = raw_input('Enter filepath (Default: ' + filepath + ')')
    if alt_filepath != '':
        filepath = alt_filepath
    return open(filepath, 'w')
```

Microprocessor

Illustrated microprocessor 44 controls and/or configures the unit 42 and/or the constituent elements thereof. The microprocessor 44 can perform any number of functions, as will appreciated by a person skilled in the art, depending on the particular application for which the sensing devices 40 are used. By way of non-limiting example, the microprocessor 44 can power-up, power-down, "sleep," reset, pair/unpair, and/or set operational parameters (including, level setting) for unit 42, module 46 and/or sensors 40a-40d. By way of further example, microprocessor 44 can effect software, control parameter and/or data transfer between digital data processor 60 and unit 42, module 46 and/or sensors 40a-40d.

Thus, for example, in order to extend the life of the battery 48, the microprocessor 44 can configure sensing devices 40 and/or communications module 48 to enter sleep mode during non-use or inactivity, e.g., if the communication module 46 is unable to connect to the digital data processor 60 for a pre-determined time (e.g., five minutes), in response to a command from that processor 60, in response to a user deactivation command (e.g., a triple-tap on the skateboard 20). And, by way of further example, the microprocessor 44 can configure the communications module 48 to operate in lower power mode when practical. To further extend battery 48 life, the microprocessor 44 preferably activates the sensing devices 40 independently of the communication module.

As will be appreciated by those skilled in the art, various ones of the control and/or configuration operations attributed to the microprocessor 44 may be handled via other functionality in the module 42. Thus, for example, one or more parameters may be burned into read-only memory modules (not shown) provided with the unit 42, may be "hardwired" into circuitry of the PCB, or otherwise, all consistent with the teachings hereof.

By way of further example, microprocessor 44 can perform data conditioning (e.g., normalization), data reduction, data compression and other preprocessing of data from sensors 40a-40d before it is sent to digital data processor 60. It can also detect fault in operation of the unit 42, module 46 and/or sensors 40a-40d, forcing notification to digital data processor 60 and/or to an operational LED and/or display panel (not shown) and/or audio output of unit 42 in case of such detection.

In some embodiments, processing of data generated by sensors 40a-40d is the province of separate digital data processor 60. In embodiments that support trick detection, such as the illustrated embodiment, that function is performed by microprocessor 44—specifically, the identification of tricks (or other feats) performed on the skateboard 20 (or other object).

The illustrated microprocessor 44 also performs control associated with such trick (feat) identification. This includes, by way of example, powering-up or waking the sensors 40a-40d in response to user activation—e.g., double-tapping of the skateboard 20 by the user. This also includes, by way of example, detecting trick (or feat) start, e.g., based on jerk detection or other characteristic changes in forces or motions measured by the sensors. And, it includes by way of example, uploading the identity of detected tricks to the digital data processor 60, e.g., along with underlying or other sensor readings.

In this latter regard, for example, the microprocessor 44 can effect uploading of the identity of an identified trick to the digital data processor 60, along with position information from a GPS sensor (not shown), time/date information from an onboard clock (not shown), max/min velocity and acceleration readings sensor 42a, and so forth—all by way of example. By way of further example, microprocessor 44 can effect uploading of a log of collected sensor readings, if it is unable to identify therefrom a particular trick—or, in some embodiments, even if it is able to identify a trick.

Instead of, or in addition to, uploading trick identity and/or underlying or other sensor readings, the microprocessor can effect notification when pre-selected trick(s) or feats—such as, in the case of skateboard 20, an "Ollie"—is/are identified. Such notification can be transmitted to the digital data processor 60. Alternatively or in addition, such notification can be effected via an alert to the aforementioned operational LED and/or display panel (not shown) of unit 42, to the aforementioned audio output module 60a, or otherwise. Indeed, such a notification can be transmitted or otherwise effected when the processor detects an attempted, but failed, trick.

Trick Detection

As noted above, in the illustrated embodiment microprocessor 44 processes of data generated by those sensors 40 to identify tricks (or other feats) performed on the skateboard 20 (or other object). An appreciation of this may be attained by reference to the discussion that follows, as well as that provided elsewhere herein. Though attributed to microprocessor 44, it will appreciated that trick (feat) detection can be performed by digital data processor 60 or other functionality, all in accord with the teachings hereof.

In the illustrated embodiment, the microprocessor 44 begins trick identification with processing data from the gyroscopes 40b-40d and accelerometers 40a is to determine what segment, or "data window", of a data stream to compare against what an expected trick signature (i.e., what a trick is expected to look like in terms of sensor data).

In order to locate such data windows, the illustrated microprocessor 44 first sets a threshold for angular displacement. If the magnitude of angular displacement sensed by the gyroscopes is beyond this threshold about any axis, microprocessor 44 considers this a potential start point of a data window in which to identify tricks.

To determine a potential end point of a data window, the microprocessor 44 sets a separate threshold on the rate of change of angular displacement. This relies on the assumption that when a trick is landed the skateboard 20 suddenly stops rotating (e.g., when it is "caught" by the user); this causes sharp fluctuations in angular displacement data.

Once a start point and end point have been identified, a final step in identifying a data window is to check that a "reasonable" amount of time has passed from the start point to the endpoint. Again, microprocessor 44 sets a threshold on the difference of the time stamp on a potential end point and the time stamp on a potential start point. If this difference is greater than the time threshold, then microprocessor 44 proceeds to compare the data in the identified data window to the signature of what is expected for each trick.

In the illustrated embodiment, there are n salient features of gyroscope and accelerometer data used to identify tricks, and each trick is assigned a collection of n-tuples. Each n-tuple assigned to a particular trick is considered a signature of that trick. If one of the signatures of a trick appears in a data window, that trick is registered as detected.

Referring back to FIGS. 1A and 1B in the illustrated embodiment, illustrated features include:

1) roll (denoted "R", in the drawing)—total angular displacement about the longest principle axis X of the skateboard given relative positioning of the sensors to the skateboard;
2) pitch P—total angular displacement about the second principle axis Y of the skateboard parallel to the ground when the skateboard is at rest on its wheels;
3) yaw ("W")—total angular displacement about the principle axis Z of the skateboard perpendicular to the ground when the skateboard is at rest on its wheels;
4) acceleration—acceleration detected along the longest axis X of the skateboard;
5) initial pitch—the sign of the pitch P detected nearest the start point of the data window. In the drawing, that sign is indicated by "+" and "−" signs adjacent ends of the curved arrow denoting the pitch P.

Each of these features, or "parameters," is bounded by thresholds and has between three and six modes. Referring to FIG. 3, the gray areas indicate the thresholds within which a given trick rotating about the longest principle axis (having roll) would be recognized.

Each of these parameters assumes a value specifying what range, given threshold, certain aspects of gyroscope and accelerometer data fall in. Each combination of values for each parameter unambiguously specifies a the type of motion a skateboard has undergone during a data window, whether it be a trick or not.

Parameter (1) reflects how much roll, if any, the skateboard rotates through during the data window. Practically, this is measuring how much kickflip or heelflip has happened during a trick. Notice that any trick that does not rotate primarily about a principle axis necessarily has some non-zero roll. Also, the skateboard rotates most easily about its longest principle axis, since the skateboard has the smallest moment of inertia in this dimension. For these reasons, parameter (1), unlike parameters (2) and (3), is useful for identifying and differentiating tricks that rotate about a single principle axis (namely the longest axis of the skateboard) and tricks that combine rotations about more than one principle axis, such as a varial flip or a 360 flip. The angular velocity in roll is roughly constant for the bulk of a given data window, and the thresholds on parameter (1) determine practically how many kickflip or heelflip rotations have occurred during the course of trick.

Parameter (2) is similar to (1), but reflects the amount of pitch the skateboard rotates through during the data window. Parameter (2) differs from (1) in that it is only useful in determining if rotation about a single principle axis is enough for a trick to have been completed. Practically, this amounts to determining whether a data window contains data for an impossible or a front foot impossible. Tricks that rotate about a non-principle axis do make gyroscopes register pitch, but in a non-obvious way. This behavior is addressed by parameter (4).

Parameter (3) is entirely similar to parameter (2), save that the information it encodes is the angular displacement about the third principle axis, or yaw. Practically this amounts to determining whether a data window contains data for a shuvit, frontside or backside, and how much. Again, for tricks that rotate about a non-principle axis yaw exhibit non-obvious behavior and captured by parameter (4).

For tricks that rotate about a non-principle axis, as reasoned above, rotation about the longest principle axis happens the fastest. Since the gyroscopes are fixed to the skateboard, this means that during the course of a trick the angular velocity registered by the sensors about, say, the principle axis corresponding to yaw will exhibit sinusoidal behavior; likewise for pitch. This makes physical sense, yet confounds the intuition of the typical skateboarder. For example, conventionally a varial flip is described as 360 degrees of roll (a kickflip) combined with 180 degrees of yaw (a shuvit). However, gyroscope data taken during the course of a varial flip results in roughly 360 degrees of roll and two out of phase sinusoids for pitch and yaw. Difficulty arises when one tries to distinguish tricks which conventionally differ by a 180 degree rotation in yaw, for example the varial flip and the 360 flip (360 degrees in roll and 360 degrees in yaw). The "shape" of the gyroscope data is roughly the same, and differs mostly in the amplitudes of the sinusoids. These amplitudes do not readily yield to the same methods of setting thresholds using in parameters (1)-(3). Instead, here the microprocessor 44 exploits the asymmetric position of the sensors on the skateboard to detect centrifugal acceleration.

Parameter (4) reflects the accelerometer data from the longest axis of the skateboard. The accelerometer experiences a centrifugal acceleration that is proportional to the square of the angular velocity registered in pitch and yaw by the gyroscopes, as exemplified by the relations below:

$$v = r * \Omega$$

$$a = v^2/r$$

$$a = r^2 * \Omega^2/r.$$

In this way, the difference tricks intuitively described as being a 180 degree rotation in yaw different becomes clear. Notice that if the sensors were placed symmetrically on the body, no centrifugal acceleration would be measured and such a scheme of detection would be impossible.

Parameter (5) reflects the initial direction of pitch: either positive, negative or zero. Practically, this determines the "stance" from which a trick is executed, either regular (negative) or nollie (positive) or the trick does not pop off the ground (zero).

Code

Software of the type suitable for execution by microprocessor 44 to effect trick detection in accord with the foregoing is provided below. It will be appreciated that this represents but one technique for configuring the microprocessor 44 to support such detection and that other techniques so configuring the microprocessor are within the scope of the invention.

```
#TrickRec.py

import socket
from IMUcommBT import *
from math import *
import time
import numpy as np
import string
#import matplotlib.pyplot as plt
import os
def emptyBuffers(bufsize):
    time_buffer = np.zeros(bufsize)
    omega_buffer = np.zeros((3, bufsize))
    accel_buffer = np.zeros((3, bufsize))
    return time_buffer, omega_buffer, accel_buffer
def fillBuffers(IMU_Socket, bufsize):
    time_buffer = np.zeros(bufsize)
    omega_buffer = np.zeros((3, bufsize))
    accel_buffer = np.zeros((3, bufsize))
    i = 0
    while(i < bufsize):
        packet = parse(IMU_Socket.recv(4096))
        num_lines = packet[0]
        for line in packet[1][0:num_lines]:
            timestamp = line[0]
            omega = line[1:4]
            accel = line[4:]
            if timestamp != -1: # (valid line) implies (timestamp != -1)
                for j in range(3):
                    time_buffer[i] = timestamp
                    omega_buffer[j, i] = omega[j]
                    accel_buffer[j, i] = accel[j]
            i = (i+1)
            if i >= bufsize: break
    return time_buffer, omega_buffer, accel_buffer
def updateBuffers(IMU_Socket, buffers, new_lines=1):
    old_time_buffer, old_omegabuffer, old_accel_buffer = buffers
    new_time_buffer, new_omega_buffer, new_accel_buffer = fillBuffers
        (IMU_Socket, new_lines)
    bufsize = len(old_time_buffer)
    omega_buffer = np.zeros((3, bufsize))
    accel_buffer = np.zeros((3, bufsize))
    time_buffer = np.concatenate((old_time_buffer[new_lines:],
        new_time_buffer))
    for i in range(3):
        omega_buffer[i] = np.concatenate((old_omega_buffer[i][new_lines:],
            new_omega_buffer[i]))
        accel_buffer[i] = np.concatenate((old_accel_buffer[i][new_lines:],
            new_accel_buffer[i]))
    return time_buffer, omega_buffer, accel_buffer
def getAverages(buffers):
    time_buffer, omega_buffer, accel_buffer = buffers
    bufsize = len(time_buffer)
    dt = np.diff(time_buffer)
    ave_dt = np.sum(dt)/(bufsize - 1)
    omega_sum = np.zeros((3))
    accel_sum = np.zeros((3))
    for i in range(3):
        omega_sum[i] = np.sum(omega_buffer[i])
        accel_sum[i] = np.sum(accel_buffer[i])
    ave_omega = omega_sum/bufsize
    ave_accel = accel_sum/bufsize
    return ave_dt, ave_omega, ave_accel
def getRanges(buffers):
    time_buffer, omega_buffer, accel_buffer = buffers
    time_range = time_buffer[-1] - time_buffer[0]
    omega_range = np.zeros(3)
    accel_range = np.zeros(3)
    for i in range(3):
        omega_range[i] = max(omega_buffer[i]) - min(omega_buffer[i])
        accel_range[i] = max(accel_buffer[i]) - min(accel_buffer[i])
    return time_range, omega_range, accel_range
def subtractAverages(buffers, ave_omega, ave_accel):
    time_buffer, raw_omega_buffer, raw_accel_buffer = buffers
    bufsize = len(time_buffer)
    omega_buffer = np.zeros((3, bufsize))
    accel_buffer = np.zeros((3, bufsize))
    for i in range(3):
        omega_buffer[i] = raw_omega_buffer[i] - ave_omega[i]
        accel_buffer[i] = raw_accel_buffer[i] - ave_accel[i]
    return time_buffer, omega_buffer, accel_buffer
```

```
def testInitialConditions(buffers):
    ave_dt, ave_omega, ave_accel = getAverages(buffers)
    time_range, omega_range, accel_range = getRanges(buffers)
    omega_test = (ave_omega[0] > 1620) and (ave_omega[0] < 1730) and\
                 (ave_omega[1] > 1620) and (ave_omega[1] < 1730) and\
                 (ave_omega[2] > 1620) and (ave_omega[2] < 1730) and\
                 (omega_range[0] < 50) and\
                 (omega_range[1] < 50) and\
                 (omega_range[2] < 50)
    accel_test = (ave_accel[0] > -50) and (ave_accel[0] < 50) and\
                 (ave_accel[1] >-50) and (ave_accel[1] < 50) and\
                 (ave_accel[2] >200) and (ave_accel[2] < 300) and\
                 (accel_range[0] < 60) and\
                 (accel_range[1] < 60) and\
                 (accel_range[2] < 60)
    return omega_test, accel_test
def interpolateBuffers(buffers):
    raw_time_buffer, raw_omega_buffer, raw_accel_buffer = buffers
    interp_bufsize = raw_time_buffer[-1] - raw_time_buffer[0]
    if (interp_bufsize > 10000):
        print "buffer overload"
    interp_time_buffer = np.arange(interp_bufsize)
    interp_omega_buffer = np.zeros((3, interp_bufsize))
    interp_accel_buffer = np.zeros((3, interp_bufsize))
    offset_time_buffer = raw_time_buffer - raw_time_buffer[0]
    for i in range(3):
        interp_omega_buffer[i] = np.interp(interp_time_buffer, off-
            set_time_buffer, raw_omega_buffer[i])
        interp_accel_buffer[i] = np.interp(interp_time_buffer, off-
            set_time_buffer, raw_accel_buffer[i])
    return interp_time_buffer, interp_omega_buffer, interp_accel_buffer
def plotBuffers(buffers, initialize = 0, start = 0, end = 0):
    time_buffer, omega_buffer, accel_buffer = buffers
    fig = plt.figure( )
    ax1 = fig.add_subplot(111)
    ax1.plot (time_buffer, omega_buffer[0], ', ', color = 'blue', alpha = 0.8)
    ax1.plot (time buffer, omega_buffer[1], ', ', color = 'orange', alpha =
        0.8)
    ax1.plot(time_buffer, omega_buffer[2], ', ', color = 'yellow', alpha =
        0.8)
    ax1.set_xlabel('time (ms)')
    ax1.set_ylabel('omega')
    ax2 = ax1.twinx( )
    ax2.plot(time_buffer, accel_buffer[0], ', ', alpha = 0.8)
    ax2.plot(time_buffer, accel_buffer[1], ', ', alpha = 0.8)
    ax2.plot(time_buffer, accel_buffer[2], ', ', alpha = 0.8)
    ax2.set_ylabel('accel')
    ax2.axvline(x = start, linewidth = 1, color = 'black', alpha = 0.2)
    ax2.axvline(x = end, linewidth = 1, color = 'black', alpha = 0.2)
    if (initialize == 0):
        plt.draw( )
        fig.savefig('_tmp_window.png', dpi = 500)
        os.system("eog_tmp_window.png")
def saveBuffers(buffers, trick):
    time_buffer, omega_buffer, accel_buffer = buffers
    print " "
    print "Detected: " + trick
    correct = ""
    while ((correct != "y") and (correct != "n")):
        correct = raw_input("Correct(y/n)?")
    if (correct == "y"):
        np.savetxt("./data/" + trick.replace(' ', '_') + "_time_buffer_" +
            time.strftime('D%Y%m%dT%H%M%S') + ".txt", time_buffer)
        np.savetxt("./data/" + trick.replace(' ', '_') + "_omegabuffer_" +
            time.strftime('D%Y%m%dT%H%M%S') + ".txt", omega_buffer)
        np.savetxt("./data/" + trick.replace(' ', '_') + "_accel_buffer_" +
            time.strftime('D%Y%m%dT%H%M%S') + ".txt", accel_buffer)
        print "Saved: " + trick + "."
    if (correct == "n"):
        trick_matrix = \
        [["not a trick", "backside powerslide", "backside 360
            powerslide", "frontside powerslide", "frontside 360 power-
            slide"],
         ["ollie", "backside shuvit", "backside 360
            shuvit", "frontside shuvit", "frontside 360 shuv-
            it"],
         ["kickflip", "varial flip", "360 flip",
            "hardflip", "360 hardflip"],
         ["heelflip", "inward heelflip", "360 inward
            heelflip", "varial heel", "360 heelflip"],
         ["double flip", "varial double flip", "360 double
            flip", "hard double flip", "360 hard double
            flip"],
         ["double heel", "inward double heel", "360 inward dou-
            ble heel", "varial double heel", "360 double heel"],
         ["not a trick", "not a trick", "impossible",
            "not a trick", "front foot impossible"],
         ["nollie", "nollie backside shuvit", "nollie backside
            360 shuvit", "nollie frontside shuvit", "nollie frontside 360
            shuvit"],
         ["nollie kickflip", "nollie varial flip", "nollie 360
            flip", "nollie hardflip", "nollie 360 hard-
            flip"],
         ["nollie heelflip", "nollie inward heelflip", "nollie 360 in-
            ward heelflip", "nollie varial heel", "nollie 360
            heelflip"],
         ["nollie double flip", "nollie varial double flip", "nollie 360 dou-
            ble flip", "nollie hard double flip", "nollie 360 hard dou-
            ble flip"],
         ["nollie double heel", "nollie inward double heel", "nollie 360 in-
            ward double heel", "nollie varial double heel", "nollie 360 double
            heel"],
         ["not a trick", "not a trick", "nollie impossi-
            ble", "not a trick", "nollie front foot
            impossible"]]
        # printing all the tricks
        longest_matrix = [0]*5
        for row in trick_matrix:
            row_length = 0
            for col in range(len(row)):
                if longest_matrix[col] < len(row[col]):
                    longest matrix[col] = len(row[col])
        print " "*4 + "0" + " "*(longest_matrix[0]+1) + \
              "1" + " "*(longest_matrix[1]+1) + \
              "2" + " "*(longest_matrix[2]+1) + \
              "3" + " "*(longest_matrix[3]+1) + \
              "4" + " "*(longest_matrix[4]+1)
        for i in range(13):
            what_to_print = str(i) + " "*(2 - len(str(i)))
            for j in range(5):
                what_to_print = what_to_print + " " + trick_matrix[i][j]
                for k in range(longest_matrix[j] - len(trickmatrix[i][j])):
                    what_to_print = what_to_print + " "
            print what_to_print
        # asking what the trick was and saving
        row = int(raw_input("row? "))
        col = int(raw_input("col? "))
        trick = trick_matrix[int(row)] [int(col)]
        np.savetxt("./data/" + trick.replace(' ', '_') + "_time_buffer_" +
            time.strftime('D%Y%m%dT%H%M%S') + ".txt", time_buffer)
        np.savetxt("./data/" + trick.replace(' ', '_') + "omega_buffer_"+
            time.strftime('D%Y%m%dT%H%M%S') + ".txt", omega_buffer)
        np.savetxt("./data/" + trick.replace(' ', '_') + "accel_buffer_" +
            time.strftime('D%Y%m%dT%H%M%S') + ".txt", accel_buffer)
        print "Saved: " + trick + "."
def detectWindow(buffers):
    raw_time_buffer, raw_omega_buffer, raw_accel_buffer = buffers
    interp_time_buffer, interp_omega_buffer, interp_accel_buffer = \
        interpolateBuffers((raw_time_buffer, raw_omega_buffer,
            raw_accel_buffer))
    interp_bufsize = interp_time_buffer[-1] - interp_time_buffer[0]
    max_trick_len = 1000 #milliseconds
    min_trick_len = 100
    start_pad_len = interp_bufsize - max_trick_len
    omega_start_thresh = 60
    omega_end_thresh = 12
    for i in range(3):
        if (abs(interp_omega_buffer[i][start_pad_len]) > omega_start_thresh):
            for t in range(max_trick_len - min_trick_len):
                for j in range(3):
                    if (abs(interp_omega_buffer[j][start_pad_len +
                        min_trick_len + t] \ -
                            interp_omega_buffer[j][start_pad_len +
                            min_trick_len + t - 1]) > omega_end_thresh):
                        trick_length = t + min_trick_len
                        trick_start = start_pad_len
                        return trick_length, trick_start
    return 0, -1
```

```
def identifyTrick(omega_window, accel_window):
    trick_list = \
    ["frontside powerslide",
    "backside powerslide",
    "frontside 360 powerslide",
    "backside 360 powerslide",
    "ollie",
    "nollie",
    "kickflip",
    "double flip",
    "varial",
    "varial double flip",
    "hardflip",
    "hard double flip",
    "360 flip",
    "360 double flip",
    "360 hardflip",
    "360 hard double flip",
    "nollie flip",
    "nollie double flip",
    "nollie varial flip",
    "nollie varial double flip",
    "nollie hardflip",
    "nollie hard double flip",
    "nollie 360 flip",
    "nollie 360 double flip",
    "nollie 360 hardflip",
    "nollie 360 hard double flip",
    "index trick",
    "heelflip",
    "double heel",
    "varial heel",
    "varial double heel",
    "inward heel",
    "inward double heel",
    "360 heel",
    "360 double heel",
    "360 inward heel",
    "360 inward double heel",
    "nollie heelflip",
    "nollie double heel",
    "nollie varial heel",
    "nollie varial double heel",
    "nollie inward heel",
    "nollie inward double heel",
    "nollie 360 heel",
    "nollie 360 double heel",
    "nollie 360 inward heel",
    "nollie 360 inward double heel",
    "backside shuvit",
    "backside 360 shuvit",
    "nollie backside shuvit",
    "nollie backside 360 shuvit",
    "frontside shuvit",
    "frontside 360 shuvit",
    "nollie frontside shuvit",
    "nollie frontside 360 shuvit",
    "impossible",
    "nollie impossible",
    "front foot impossible",
    "nollie front foot impossible"]
    trick = ""
    theta_180 = 57000
    theta_360 = 87000
    accel_180 = 160000
    accel_360 = 450000
    theta_thresh = 30000
    accel_thresh = 100000
    pitch_thresh = 40
    trick_vector = np.zeros((5))
    bufsize = len(omegawindow[0])
    #d_theta = np.zeros((3, bufsize-1))
    #d_velocity = np.zeros((3, bufsize-1))
    d_theta = np.zeros((3, bufsize))
    d_velocity = np.zeros((3, bufsize))
    initial_pitch = 0
    theta = np.zeros(3)
    velocity = np.zeros(3)
    #dt = omegadiff[i][0]
    for i in range(3):
        #d_theta[i] = np.diff(omega_window[i], axis = 0)
        #d_velocity[i] = np.diff(accel_window[i], axis = 0)
        d_theta[i] = omega_window[i]
        d_velocity[i] = accel_window[i]
        theta[i] = np.sum(d_theta[i])
        velocity[i] = np.sum(d_velocity[i])
    # find initial pitch direction
    for i in range(bufsize-1):
        if (abs(omega_window[1][i]) >pitch_thresh):
            initial_pitch = omega_window[1][i]
            break
    #first coordinate of trick, determining direction of and how much, if
        any, flip
    if (theta_180-theta_thresh)<theta[0]<(theta_180+theta_thresh):
        trick_vector[0] = ½
    if (-theta_180-theta_thresh)<theta[0]<(-theta_180+theta_thresh):
        trick_vector[0] = -½
    if (2*theta_180-theta_thresh)<theta[0]<(2*theta_180+theta_thresh):
        trick_vector[0] = 1
    if (-2*theta_180-theta_thresh)<theta[0]<(-2*theta_180+theta_thresh):
        trick_vector[0] = -1
    if (4*theta_180-2*theta_thresh)<theta[0]<(4*theta_180+2*theta_thresh):
        trick_vector[0] = 2
    if (-4*theta_180-2*theta_thresh)<theta[0]<(-
        4*theta_180+2*theta_thresh):trick_vector[0] = -2
    if (-theta_thresh)<theta[0]<(theta_thresh):
        trick_vector[0] = 0
    #second coordinate of trick, determining direction of and how much impos-
        sible
    if (2*theta_180-theta thresh)<theta[1]<(2*theta_180+theta_thresh):
        trick_vector[1] = 1
    if (-2*theta_180-theta_thresh)<theta[1]<(-2*theta_180+theta_thresh):
        trick_vector[1] = -1
    if (-thetathresh)<theta[1] <(theta_thresh):
        trick_vector[1] = 0
    #third coordinate of trick, determining direction of and how much inde-
        pendent shuvit
    if (2*theta_180-theta_thresh)<theta[2]<(2*theta_180+theta_thresh):
        trick_vector[2] = 2
    if (-2*theta_180-theta_thresh)<theta[2]<(-2*theta_180+theta_thresh):
        trick_vector[2] = -2
    if (1*theta_180-theta_thresh)<theta[2]<(1*theta_180+theta_thresh):
        trick_vector[2] = 1
    if (-1*theta180-theta_thresh)<theta[2]<(-1*theta_180+theta_thresh):
        trick_vector[2] = -1
    if (-theta_thresh)<theta[2]<(theta_thresh):
        trick_vector[2] = 0
    #fourth coordinate of trick, measuring centrifugal acceleration and de-
        termining dependent behavior of pitch and yaw in combinatory
        tricks
    if (accel_360-accel_thresh)<(velocity[0])<(accel_360+accel_thresh):
        trick_vector[3] = 2
    if (-accel_360-accel_thresh)<(velocity[0])<(-accel_360+accel_thresh):
        trick_vector[3] = -2
    if (accel_180-accel_thresh)<(velocity[0])<(accel_180+accel_thresh):
        trick_vector[3] = 1
    if (-accel_180-accel_thresh)<(velocity[0])<(-accel180+accel_thresh):
        trick_vector[3] = -1
    if (-accel_thresh)<velocity[1]<(accel_thresh):
        trick_vector[3] = 0
    #fifth coordinate of trick, determining regular or nollie stance
    if pitch_thresh<initial_pitch:
        trick_vector[4] = 1
    if initial_pitch<-pitch_thresh:
        trick_vector[4] = -1
    if (-pitch_thresh)<initial_pitch<pitch_thresh:
        trick_vector[4] = 0
    trick_vector = list(trick_vector)
    # Trick detection
    if trick_vector == [0, 0, -1, 0, 0] : trick = trick_list[0]
    if trick_vector == [0, 0, 1, 0, 0] : trick = trick_list[1]
    if trick_vector == [0, 0, -2, 0, 0] : trick = trick_list[2]
    if trick_vector == [0, 0, 2, 0, 0] : trick = trick_list[3]
    # if trick_vector == [0, 0, 0, 0, -1] : trick = trick_list[4]
    # if trick_vector == [0, 0, 0, 0, 1] : trick = trick_list[5]
    if trick_vector == [-1, 0, 0, 0, -1] : trick = trick_list[6]
    if trick_vector == [-2, 0, 0, 0, -1] : trick = trick_list[7]
    if trick_vector == [-1, 0, 0, -1, -1] : trick = trick_list[8]
```

-continued

```
if trick_vector == [−2, 0, 0, −1, −1] : trick = trick_list[9]
if trick_vector == [−1/2, 0, 0, 1, −1] : trick = trick_list[10]
if trick_vector == [−2, 0, 0, 1, −1] : trick = trick_list[11]
if trick_vector == [−1, 0, 0, −2, −1] : trick = trick_list[12]
if trick_vector == [−2, 0, 0, −2, −1] : trick = trick_list[13]
if trick_vector == [−1, 0, 0, 2, −1] : trick = trick_list[14]
if trick_vector == [−2, 0, 0, 2, −1] : trick = trick_list[15]
if trick_vector == [−1, 0, 0, 0, 1] : trick = trick_list[16]
if trick_vector == [−2, 0, 0, 0, 1] : trick = trick_list[17]
if trick_vector == [−1, 0, 0, 1, 1] : trick = trick_list[18]
if trick_vector == [−2, 0, 0, 1, 1] : trick = trick_list[19]
if trick_vector == [−1, 0, 0, −1, 1] : trick = trick_list[20]
if trick_vector == [−2, 0, 0, −1, 1] : trick = trick_list[22]
if trick_vector == [−1, 0, 0, 2, 1] : trick = trick_list[23]
if trick_vector == [−2, 0, 0, 2, 1] : trick = trick_list[24]
if trick_vector == [−1, 0, 0, −2, 1] : trick = trick_list[25]
if trick_vector == [−2, 0, 0, −2, 1] : trick = trick_list[26]
if trick_vector == [1, 0, 0, 0, −1] : trick = trick_list[27]
if trick_vector == [2, 0, 0, 0, −1] : trick = trick_list[28]
if trick_vector == [1, 0, 0, 1, −1] : trick = trick_list[29]
if trick_vector == [2, 0, 0, 1, −1] : trick = trick_list[30]
if trick_vector == [1, 0, 0, −1, −1] : trick = trick_list[31]
if trick_vector == [2, 0, 0, −1, −1] : trick = trick_list[32]
if trick_vector == [1, 0, 0, 2, −1] : trick = trick_list[33]
if trick_vector == [2, 0, 0, 2, −1] : trick = trick_list[34]
if trick_vector == [1, 0, 0, −2, −1] : trick = trick_list[35]
if trick_vector == [2, 0, 0, −2, −1] : trick = trick_list[36]
if trick_vector == [1, 0, 0, 0, 1] : trick = trick_list[37]
if trick_vector == [2, 0, 0, 0, 1] : trick = trick_list[38]
if trick_vector == [1, 0, 0, −1, 1] : trick = trick_list[39]
if trick_vector == [2, 0, 0, −1, 1] : trick = trick_list[40]
if trick_vector == [1, 0, 0, 1, 1] : trick = trick_list[41]
if trick_vector == [2, 0, 0, 1, 1] : trick = trick_list[42]
if trick_vector == [1, 0, 0, −2, 1] : trick = trick_list[43]
if trick_vector == [2, 0, 0, −2, 1] : trick = trick_list[44]
if trick_vector == [1, 0, 0, 2, 1] : trick = trick_list[45]
if trick_vector == [2, 0, 0, 2, 1] : trick = trick_list[46]
if (trick_vector == [0, 0, −1, 0, −1] ) or (trick_vector == [0, 0, 0, −1, −1]) :
    trick = trick_list[47]
if trick_vector == [0, 0, −2, 0, −1] : trick = trick_list[48]
if (trick_vector == [0, 0, 1, 0, 1] ) or (trick_vector == [0, 0, 0, 1, 1]):
    trick = trick_list[49]
if trick_vector == [0, 0, 2, 0, 1] : trick = trick_list[50]
if (trick_vector == [0, 0, 1, 0, −1]) : trick = trick_list[51]
if trick_vector == [0, 0, 2, 0, −1] : trick = trick_list[52]
if trick_vector == [0, 0, −1, 0, 1] : trick = trick_list[53]
if trick_vector == [0, 0, −2, 0, 1] : trick = trick_list[54]
if (trick_vector == [0, −1, 0, 0, −1]) or (trick_vector == [0, 0, −1, −2, −1]):
    trick = trick_list[55]
if trick_vector == [0, 1, 0, 0, 1] : trick = trick_list[56]
if trick_vector == [0, 1, 0, 0, −1] : trick = trick_list[57]
if trick_vector == [0, −1, 0, 0, 1] : trick = trick_list[58]
if trick == "" : trick = "not a trick"
print initial_pitch, theta, velocity
print "trick_vector = " + str(trick_vector)
print trick
return trick
```

Software of the type suitable for execution by microprocessor 44 to test operation of a module 42 constructed in accord with the teachings hereof is provided below. It will be appreciated that this represents but one technique for configuring the microprocessor 44 to support such testing are within the scope of the invention.

```
# test.py

#!/usr/bin/python
import socket
from IMUcommBT import *
from TrickRec import *
from math import *
import time
import numpy as np
import string
plot_windows = False
save_buffers = False
bufsize = 256
address = '00:06:66:42:94:8E'
print "connecting to flyriser..."
IMU_Socket = getIMUsocket(address)
print "done."
def flushBluetoothBuffer( ):
    IMU_Socket.recv(1000000)
def main( ):
    ## calibrate initial sensor offsets
    IMU_Socket.send("1")
    flushBluetoothBuffer( )
    print " "
    print "calibrating flyriser...put board into upright resting position."
    omega_test, accel_test = True, True
    buffers = fillBuffers(IMU_Socket, bufsize)
    omega_test, accel_test = testInitialConditions(buffers)
    while not(omega_test and accel_test):
        buffers = fillBuffers(IMU_Socket, bufsize)
        omega_test, accel_test = testInitialConditions(buffers)
        print "board is either not upright or is moving!!!"
    ave_dt, ave_omega, ave_accel = getAverages(buffers)
    print "done."
    print " "
    IMU_Socket.send("0")
    IMU_Socket.send("1")
    flushBluetoothBuffer( )
    while True:
        buffers = updateBuffers(IMU_Socket, buffers, 1)
        offset_buffers = subtractAverages(buffers, ave_omega,
        ave_accel)
        trick_length, trick_start = detectWindow(offset_buffers)
        if(trick_length != 0):
            IMU_Socket.send("0")
            start, end = trick_start, trick_start + trick_length
            interp_time_buffer, interp_omega_buffer,
interp_accel_buffer = InterpolateBuffers(offset_buffers)
            omega_window = np.zeros((3, trick_length))
            accel_window = np.zeros((3, trick_length))
            for dim in range(3):
                omega_window[dim] =
                    interp_omega_buffer[dim][start:end]
                accel_window[dim] =
                    interp_accel_buffer[dim][start:end]
            trick = identifyTrick(omega_window, accel_window)
            print "trick_length = " + str(trick_length)
            print "trick_start = " + str(trick_start)
            print "trick_end = " + str(trick_start + trick_length)
            print "averages:"
            print getAverages(buffers)
            print "ranges:"
            print getRanges(buffers)
            if plot_windows:
                flushBluetoothBuffer( )
                plotBuffers(interpolateBuffers(offset_buffers), start =
trick_start, end = trick_start + trick_length)
            if save_buffers:
                saveBuffers(buffers, trick)
            flushBluetoothBuffer( )
            print "flushing..."
            IMU_Socket.send("1")
            buffers = fillBuffers(IMU_Socket, bufsize)
            print "done."
            print " "
if __name__ == '__main__':
    try:
        main( )
    finally:
        IMU_Socket.send("0")
        IMU_Socket.close( )
```

Alternative

Alternative embodiments of the invention utilize other techniques for trick identification, e.g., of the type described in aforementioned, incorporated-by-reference applications U.S. Provisional Application No. 61/514,773, filed Aug. 3, 2011, entitled "Signature-Based Trick Determination Systems and Methods for Skateboarding and Other Activities of Motion"

pending U.S. patent application Ser. No. 13/565,971, filed this same day herewith, entitled "Signature-Based Trick Determination Systems and Methods for Skateboarding and Other Activities of Motion,"

PCT Application Serial No. PCT/US2012/049423, filed this same day herewith entitled "Signature-Based Trick Determination Systems And Methods For Skateboarding And Other Activities Of Motion,"

abandoned U.S. application Ser. No. 13/197,429, filed Aug. 3, 2011, and published as US2012-0116714-A1 on May 10, 2012, entitled "Digital Data Processing Systems and Methods for Skateboarding and Other Social Sporting Activities,"

PCT Application No. PCT/US11/46423, filed Aug. 3, 2011, and published as WO 2012/018914 on Feb. 9, 2012, entitled "Digital Data Processing Systems And Methods For Skateboarding and Other Social Sporting Activities".

Digital Data Processor

Referring back to FIG. 1, data processor 60 can comprise a dedicated device (e.g., a desktop or laptop computer) or it can be part a multifunction device, e.g., as in the case of a data processor that is embedded in a cell phone, personal digital assistant, or other mobile device (collectively, "mobile device"). In the illustrated embodiment, processor 60 is in communications coupling with the unit 42 and, more particularly, for example, microprocessor 44 and/or sensing devices 40, e.g., via BLUETOOTH, WIFI, cellular, infrared, or other wireless or wired transmission medium.

In various embodiments, the data processor 60 processes data regarding skateboard 20 and, more particularly, data with sensors 40a-40d and/or the microprocessor 44 in view of scripts, guidelines, programming or other rules (collectively, "rules") and/or data that define (i) the game, sport, entertainment activity, training exercise or other endeavor for which the skateboard 20 is being used, and/or (ii) the virtual sound space in which that endeavor is exercised, and (b) driving the audio output device 60a to effect sounds embodying at least a portion that virtual sound space (e.g., in a vicinity of the actor represented by the skateboard 20 and/or its operator) and/or the skateboard operator's interaction with that virtual sound space, e.g., as he or she effects moves and/or performs tricks (or feats) with the skateboard in the real and physical space surrounding him/her. To this end and/or otherwise in connection therewith, the digital data processor performs one or more of the following functions. Such processing can be performed on the digital data processor 60 using conventional software and data analysis techniques as adapted in accord with the teachings hereof, as can the processing of data regarding the skateboard in view of rules and/or data defining the endeavor and/or the virtual sound space discussed above:

Process information received from unit 42, and still more particularly, for example, microprocessor 44 and/or sensing devices 40 to quantitatively or qualitatively characterize the motion, location and/or other characteristics of the skateboard.

Identify tricks performed on the skateboard 20 (or other object) (e.g., in embodiments where such identification is not performed by microprocessor 44 and/or in which auxiliary processing by the data processor can facilitate and/or confirm such identification). By way of non-limiting example, in one embodiment, the digital data processor 60 can supplement trick identification (if any) performed by the microprocessor by analyzing other aspects of skateboard use, e.g., maximum height attained during a skateboard session, longest time in the air during the session, fastest speed attained, longest sustained run, and so forth. It can perform one or more of the aforementioned functions with the results of these analyses, as well or instead. Of course, in some embodiments these analyses can be performed by the microprocessor 44 instead or in addition.

Log identified tricks and/or characteristics of the skateboard and/or its environment measured by the sensing devices 40.

Exchange information regarding identified tricks, measured characteristics, and/or associated information with central servers, central stores, other nodes, the Internet, and/or otherwise.

Obtain information defining the play, sport, entertainment activity or other endeavor—or, more typically, defining the positions/actions of other players, characters, obstacles, scenery, etc., that make up the virtual sound space—from external sources, e.g., other "nodes" (as discussed below), central servers, central stores, the Internet, or otherwise. This can include, for example, other skateboarders (who, too, may be equipped with a system 10), another person (whether or not on a skateboard), or any other entity (e.g., a moving vehicle, an ocean wave, and so forth).

In some embodiments, a given data processor 60 (e.g., a cell phone, PDA or computer) may be capable of operation with multiple different skateboards (or other objects) 20, concurrently or one-at-a-time. This can facilitate, for example, the use of a cell phone 60 with multiple objects (e.g., skateboards, surf boards, etc.) equipped in accord with the tachings and owned by the given user or, conversely, by multiple such objects owned by different persons (e.g., friends, competitors, etc.).

Moreover, in some embodiments, the microprocessor 44, unit 42 and/or cell phone (or digital data processor) 60 are equipped to communicate to one another and/or to central servers, central stores, and/or other nodes, the Internet, or otherwise via a mesh network, established among themselves or otherwise. This can, for example, facilitate communication among skateboards 20 in the same recreational park, e.g., when only a few of the users have cell phones.

Construction Referring back to FIGS. 1A and 1B, data processor 60 can comprise a dedicated device (e.g., a desktop or laptop computer) or it can be part of a multifunction device, e.g., as in the case of a data processor that is embedded in a cell phone, personal digital assistant, or other mobile device (collectively, "mobile device").

It includes one or more modules for the receiving, transmitting, processing, storage, generation and/or display of data of the type conventionally associated with such dedicated and/or multifunction devices, all as adapted in accord with the teachings hereof. For example, the data processor 60 can include a store that is configured and operated utilizing conventional database techniques (as adapted accord with the teachings hereof) to record information regarding identified tricks and/or characteristics of the skateboard and/or its environment measured by the sensing devices 40, e.g., for later access by the skateboard user or others.

It can also include an audio output device or module 60a that generates an audio output (e.g., a song and/or a sound or series of sounds), e.g., in response to information received from the skateboard and/or the other nodes (if any), in response to user prompts, or otherwise.

As shown in the drawing, data processor 60 is in communications coupling with the skateboard 20 and, more particularly, unit 42, and still more particularly, for example, microprocessor 44 and/or sensing devices 40, e.g., via BLUETOOTH, WIFI, cellular, infrared, or other wireless link-though, in other embodiments such coupling may be wired, instead or in addition.

In an exemplary embodiment, the digital data processor 60 is a smart phone having a communication module capable of receiving the wireless communication signals generated by the sensing device 40. The smart phone can be held, for example, in a skateboarder's pocket within transmission range of the sensing device 40. Alternatively, the digital data processor 60 can be stationary when the skateboard 20 is not. For example, the digital data processor 60 (whether a smartphone, laptop or otherwise) that is positioned in proximity to a ramp or jump on which tricks and/or other characteristics of the skateboard will be determined. In some embodiments, the sensing device 40 can buffer or store information for transmission to the digital data processor 60 until the two devices are brought within range or otherwise placed in communications coupling (e.g., via wired connection and/or user command).

Audio Output

In one embodiment, the digital data processor 60 includes an audio output module 60a that generates audio output, e.g., a song selected by the user, a pre-recorded sound, a synthesized sound, or otherwise. The module 60a may comprise one or more speakers that are embedded with microprocessor 44, e.g., on the skateboard 20, and/or that are housed separately from it, albeit coupled for communications via BLUETOOTH, infrared or other wireless or wired transmission medium. Alternatively, or in addition, module 60a can be part mobile device that is in communications coupling (e.g., via BLUETOOTH, WIFI, cellular, infrared, or other wireless or wired transmission medium, or otherwise) with the digital data processor 60. Regardless, the module 60a may arranged for mono playback, stereo playback (e.g., as via the headphones illustrated in FIG. 1) or otherwise.

Audio output may be activated by the user and its volume, duration or other characteristics controlled by way of a switch (not shown) or otherwise. Alternatively, or in addition, the audio output can be a sound or series of sounds generated in response to data received by the digital data processor 60 from the sensing device 40 regarding a trick or characteristic of the skateboard 20.

For instance, as the skateboard user performs a specific trick or the skateboard attains a certain characteristic (e.g., a pre-determined speed, height, etc.), the digital data processor 60 can control the audio output device to generate a sound or series of sounds to alert the user. For example, when unit 42 detects that the user is performing an "ollie," the digital data processor 60 can cause the audio output device to generate a loud crashing noise when the skateboarder kicks down on the back edge of the skateboard. By way of another non-limiting example, the digital data processor can cause the audio output device to generate a "whirling" sound when the skateboard 20 is being spun.

In another exemplary embodiment, digital data processor can cause the audio output device to generate an audio output (e.g., a song with a given rhythm) that is manipulated based on the characteristic(s) of the skateboard 20. By way of non-limiting example, the playback of the song can be sped up or slowed down in response to the speeding up or slowing down, respectively, of the skateboard 20. An increase in height (e.g., a jump), for example, of the skateboard 20 can amplify the high tones of the audio output, while a decrease in height (e.g., a landing) can amplify the low tones. Variations in the audio output can also prompt the user (e.g., skateboarder), for example, to perform a certain task (e.g., speed up) or alert the user to attempt a new action.

In this way, the digital data processor 60 can be used as a learning tool. In reference to a certain action desired to be performed by an skateboard, for example, the audio output device can generate audio output (e.g., a signal) to alert the user to perform a sequence of actions, or perform the next in a sequence of actions, in order to attain the desired characteristic(s).

In addition to, or in the alternative to, outputting the audio output in real-time, the digital data processor 60 can associate an audio signal with identified tricks and/or characteristics of the skateboard and/or its environment measured by the sensing devices 40. If the user (or another) subsequently accesses a stored record of that trick or other characteristic, the digital data processor 60 or other device can replay the associated audio signal—e.g., allowing the user or another to relive the occasion.

Game Play

FIG. 4 is a flowchart depicting operation of a digital data processor 60 according to one practice of the invention enabling an operator to use skateboard 20 and system 10 to engage in a voice-prompted, one-person (or "single-player") game, sport, entertainment activity, training exercise or other endeavor in a virtual sound space. For sake of simplicity and without loss of generality, the endeavor is referred to below and in the drawing as a "game."

In step 80, the user mounts the skateboard and activates the audio output device 60a. This may include activating speakers and/or inserting earphones, depending upon implementation. In embodiments where the processor 60 executes on a mobile device, the user may also choose to place that device in a pocket or backpack, e.g., to take advantage or its on-board speaker, to facilitate the transfer of information between processor 60 and unit 42, and so forth.

In step 82, the user signals the processor 60 to activate the game to be played. In embodiments where the processor 60 executes on a mobile device, this is typically done via a graphical user interface. Although in some such embodiments, as well as those in which the processor executes on a dedicated device, such activation may involve the pressing of buttons, shaking or otherwise manipulating the device, and so forth. Indeed, in some embodiments, the game may be activated upon mounting of the skateboard 20, activation of the output device, mounting or tapping on the skateboard and so forth.

In step 84, the processor 60 executes initializes software ("game-playing software") that interprets rules defining the game and the 3D virtual sound space and that drives the output device 60a to effect sounds embodying at least a portion that virtual sound space (e.g., in a vicinity of the actor represented by the skateboard 20 and/or its user) and/or the skateboard user's interaction with that virtual sound space. Initializing can include loading those rules and/or accompanying data (e.g., from memory, a central store or server, and so forth) and commanding the device 42 to initialize sensors.

In step 86, the game-playing software begins execution. This can include awaiting any user activation command indicating readiness to start the game (e.g., double-tapping on the skateboard 20). It can further include driving the output device 60a to effect a background environment of the sound space (or "soundscape") in which the game will be executed. Such a soundscape can include, by way of non-limiting example, backgrounds noises associated with a city, a ski slope, a battle field, a class room or other virtual environment in which the game is played.

In step 88, the game-playing software begins execution of the game, e.g., in response to a user activation command (again, for example, double-tapping on the skateboard). In the illustrated example of a voice-prompted game, this can include driving the audio output device to (i) include, along with the soundscape, an audio representation of a target (e.g., of a virtual player, character, obstacle, item of scenery, etc.) near to or far from the user in the virtual space and ahead, stationary or moving, beside or behind him/her—all by way of non-limiting example, and (ii) effect a voice commanding the skateboard user to take a particular action with respect to that target—for example, to skate in a designated direction, to perform a specified trick, and so forth).

In step 90, the user attempts to performs the commanded act using the skateboard 20.

In step 92, the game-playing software monitors information from unit 42, and still more particularly, for example, microprocessor 44 and/or sensing devices 40 to determine the user's progress toward performing the commanded act. This can include driving the audio output device to reflect changes in the soundscape and/or the audio representation of the target indicative of the user's progress, e.g., making the target sound closer or further, moving from one side to the other relative to the user, and so forth. It can also include sounding laser strikes, gunshots, hits, near misses and so-forth as other actors in the game interact with one another and/or with the actor represented by the user and vice versa. This can also include detecting whether the user succeeds or fails in performing the designated act, e.g., moved the skateboard as directed, performed the specified trick, and so forth.

In regard to the foregoing, the digital data processor 60 and, more particularly, the game-playing software translates the user's movements and/or tricks (feats) with the skateboard into actions by the actor represented by him in the game. Thus, for example, as the user rolls the skateboard forward in the physical world, his/her actor in the virtual sound space moves forward, with a corresponding change in the soundscape and from those other actors, obstacles, scenery, etc., therein; when the user turns the skateboard to the left in the physical world, he/she hears sounds as if his/her respective characters turned left in the virtual world; and so forth—all depending on the rules of the game. Moreover, for some games the processor and game playing software may treat tricks or feats on the skateboard 20 in the physical world as actions in the virtual sound world, e.g., touching, capturing, shooting, freeing, or taking some other action with respect to the simulated object. For example, some tricks may translate to offensive strikes (gunshots, first blows, etc.) in the virtual sound space, other tricks to defensive maneuvers, and so forth—again, all depending on the rules of the game.

In step 94, the game-playing software drives the audio output device to provide audio feedback to the user regarding his/her performance, e.g., causing that device to sound applause, boos, vocalizations of numerical ratings, etc., dependent on the user's success in performing the action, e.g., how well readings sensed by devices 40 and/or trick detected by microprocessor 44 match command issued in step 88.

In step 96, the game-playing software logs the user's performance, e.g., along with information gathered from unit 42 in step 92 and/or statistics regarding same, to a local store and/or to a central server or central store. An advantage of such logging is, for example, that it makes possible validating what games, sports or other endeavor the operator effected on the skateboard (or other object) as well, for example, as the success of that endeavor.

In step 98, the game-playing software readies for execution of the next step of the game and returns execution to step 88, or exits, depending on rules of the game.

In some embodiments, the simulated sounds of other actors, obstacles, scenery, etc., driven by the digital data processor 60 and, more particularly, game-playing software pertain to imaginary objects whose positions and/or actions are defined the rules and/or data that define (i) the game, sport, entertainment activity, training exercise or other endeavor for which the skateboard 20 is being used, and/or (ii) the virtual sound space in which that endeavor is exercised, In other embodiments, those simulated sounds (or, at least, some of them) are based on positions, actions and/or other characteristics of real-world objects, e.g., other skateboarders (who, too, may be equipped with a system 10 according to such aspects of the invention), another person (whether or not on a skateboard), or any other object (e.g., a moving vehicle, an ocean wave, and so forth).

By way of non-limiting example, in a "cloud surfer" game, the digital data processor 60 and game-playing software can generate simulated sounds of weather patterns (e.g., thunderstorms, sunny skies, etc.) in areas of the virtual sound space that correspond with regions of the country (or world) over which those weather patterns are occurring, e.g., based on measurements obtained by the digital data processor 60 in real-time (or otherwise) from a central server, a national weather service or otherwise. In such a game, the digital data processor can translate the user's actions on skateboard 20 into movement of a corresponding actor in the virtual sound space relative to those weather patterns, e.g., sounding thunder as the actor passes over the a stormy weather pattern in the virtual sound space, chirping birds as he/she passes over a sunny regions, and so forth.

By way of further non-limiting example, in a multi-player racing challenge game, the digital data processor 60 and game-playing software can generate simulated sounds of other skateboarders, skiers, rollerbladers or other competitors that compete with the user within the virtual space. Movements of those other competitors can be based on measurements obtained from a central server, central store and/or other nodes pertaining to movements by the operators of their respective skateboards. In such a game, the digital data processor can translate the user's actions on skateboard 20 into movement of a corresponding actor in the virtual sound space relative to the other players and, likewise, can translate those other player's actions on their respective systems into movement of their respective actors. Based on that, the digital data processor can drive the output device to simulate sounds of racers passing, catching up to, being passed by, or taking other actions relative to the user in the sound space. This has the advantage, for example, of allowing multiple players to compete, even if they are not near one another physically.

Example

A Sensor-Based Audio Game Using a Skateboard as a Controller

With a gyroscope and accelerometer mounted on skateboard inside a riser pad between the back truck and the deck, it is possible to use a skateboard as a BLUETOOTH controller to navigate an audio environment represented on a mobile device. Using these hardware elements, there is a general framework for developing gaming software based on the audio environment the user experiences.

The overall implementation of the game is a single large time event loop that continues until game termination. Each iteration through the loop corresponds to one set of values received from the sensors on the skateboard, an update of the objects in the virtual space, moves and rotates the environment to its new position relative to the player, update to the current score and a modification of the audio feedback That is to say, for collection of data sent to the mobile device by the hardware the virtual space/audio environment is reconfigured and all objects in it have their state updated. Not all objects may move. Note that the player can also be seen as an object and he or she may move or rotate depending on the detected movements of the skateboard and the desired effect in the game.

Essential to any embodiment conceived of thus far is the interpretation of sensor data as tricks one can execute on a skateboard. So with each time step is associated an iteration of the trick detection algorithm. Trick detection consists of first identifying the start and ending of a trick. Tricks start with the board flat on the ground, as easily determined from the accelerometer data, followed by a sharp increase in the angular velocity measured about at least one principle axis, as read from the gyroscope. The end of a trick is identified by another sharp change in angular velocity about one or more gyroscopic axes, followed by the board being flat on the ground.

The game play specifies which trick or set of tricks are applicable at any point in time. Trick detection provides a score or accuracy of each trick based on the sensor data in the trick window. In pseudocode:

```
Foreach trick in WatchedForTricks:
    TrickScore[trick] = detectTrick( trickSensorWindow , trick )
If maximum score over all WatchedForTricks < minimum trick score
threshold:
    return FAILED
Else return pair trick and score of the maximum scoring trick    in
set
    WatchedForTricks
```

With this framework in place, pseudocode representing an active game may look something like:

```
Perform trick detection step using previous K time steps and
depending on state
        case WaitingForTrickStart:
                allocate a SensorWindowBuffer to hold sensor
        data needed to identify trick state becomes
    DetectingTrick
        case DetectingTrick:
                add sensor input to trick detection buffer if
        end-of-trick detected, state becomes
    TrickCompleted
        case TrickCompleted:
                identify trick using SensorDataWindow and
            ExpectedTricks
                update player object trick status; state becomes
                waitForTrickStart
```

Objects have position in the audio environment indicated by a characteristic sound/set of characteristic sounds. At each time step, this sound is modified based on the relative distance between object and the player as well as the angle between the front of the player and the position of the object. These quantities are computed based on the sensor readings from the hardware embedded in the riser pad.

To each object there are also associated "Triggers"; certain classes of sensor data that effect the behavior and state of a given object. A trigger will typically be a combination of detected tricks and position relative to the player. For example, a trigger for a particular object might be a successfully landed kickflip with position in line with that of the player and within a certain distance. In this case if the player "faces" the object (i.e. rotates the audio environment so that the front of the player object is turned toward the object with this trigger) and successfully lands a kickflip, the object's state would change in a prescribed way, such as losing a unit of health.

In pseudo-code, we have for example:

```
foreach object:
        update the position of the object, i.e. location and
        heading, based on current location, heading, and
        current linear and angular velocity
foreach object OBJ:
        if trigger T of OBJ evaluates to true:
        perform action associated with T for OBJ update
    health of OBJ
foreach object OBJ:
        produce sound of T based on its location, health, and
    action
```

There is a data structure associated with each object. The set of objects specifies a specific level of the game. The purpose of an early level of the game is to 1) familiarize the player with how to navigate space with a skateboard using audio information as feedback, and 2) provide a basic framework of how the player can interact with various types of objects in his environment. What follows is a description of a simple level design from a game player's perspective that attempts to fulfill the above requirements while gently easing the player into the standard format of play.

The initial level consists of a small number of segments or waves. Each wave has a set of enemies and power-ups. e.g. objects, that the player must destroy and collect, respectively, in order to trigger the next wave.

In the first wave the player only encounters one type of object: the simplest type of enemy. The simplest of tricks kills it. It has only one unit of health and is susceptible to all forms of attack (i.e. any trick performed once will kill it). Six of these basic enemies comprise the first wave. Each enemy attacks one at a time and takes a linear path toward the position of the player. If the player is touched by the enemy the player loses one unit of health. Once the player successfully lands a trick while facing the enemy it dies and the next enemy approaches from a fixed relative position. After the player has defeated all six basic enemies wave one is finished.

Wave two is simply one item that when touched by the player restores his health by one unit. No trick is required to interact with this object; the required buffer data is simply alignment with the player and proximity. The player simply needs to turn and face the item as it moves linearly toward him. Failure to do so results in having to proceed to the third wave with all the damages acquired during the first wave.

The third and final wave is a boss. Just like the basic enemies of the first wave, all tricks successfully completed while facing the boss decrease its health by one unit. However, differing from the basic enemies the boss has a total of three units of health and instead of advancing toward the player on a line the boss slowly spirals toward the player. When the player successful attacks the boss, it resets to a default distance and begins the spiral again. The boss also resets position if the player fails to attack it and the boss touches the player reducing the player's health by one unit.

Pseudocode for this scenario might look something like this:

```
#data needed to define all the objects of level one
    player_data = trick_data(roll, min_bound, 6)
    enemy_data = trick data(ollie, max_bound, 1)
    item_data = trick_data(roll, min_bound, 0)
    boss_data = trick_data(ollie, max_bound, 4)
#the objects of level one
    player = object(player_data, r=0, 0, null, sample_1)
    basic_enemy = object(enemy_data, theta=c_1, 1, min_volume,
        sample_2)
    plus_health = object(item_data, theta=c_2, -1, max_volume,
        sample_3)
    boss_enemy = object(boss_data, r=theta, 1, min_volume,
        sample_4)
#the three waves of level one
    first_wave = wave((basic_enemy, 6, 2*pi/5))
    second_wave = wave((plus_health, 1, 0))
    third_wave = wave((boss_enemy, 1, 0))
```

MultiNodal System

A system 10 of the type shown in FIGS. 1A and 1B and described above can form one "node" in a larger system that includes, in addition to system 10, one or more other such systems. The respective microprocessors 44 and/or digital data processors 60 of those systems may communicate with one another on a peer-to-peer basis. Alternatively, or in addition, those systems may be coupled to a central store for logging of identified tricks, skateboard characteristics and/or associated information generated by the systems 10. Moreover, they may be coupled to a central server that facilitates the exchange of such tricks, characteristics and/or associated information between the nodes, e.g., in support of a social network, to facilitate competitions or otherwise, as discussed by way of example in incorporated-by-reference PCT Application No. PCT/US11/46423, filed Aug. 3, 2011, and published as WO 2012/018914 on Feb. 9, 2012, entitled "Digital Data Processing Systems And Methods For Skateboarding and Other Social Sporting Activities," and abandoned U.S. application Ser. No. 13/197,429, filed Aug. 3, 2011, and published as US-2012-0116714-A1 on May 10, 2012, entitled "Digital Data Processing Systems and Methods for Skateboarding and Other Social Sporting Activities," both of which PCT and US applications claim the benefit of priority of U.S. Provisional Patent Application Ser. No. 61/370,439, filed Aug. 3, 2010, U.S. Provisional Patent Application Ser. No. 61/371,161, filed Aug. 5, 2010, and U.S. Provisional Patent Application Ser. No. 61/386,207, filed Sep. 24, 2010. Reference is had in these particular regards and by way of non-limiting example, to the system 10' shown in FIG. 4 of those respective applications and discussed in the accompanying text thereof.

CONCLUSION

Described above are methods and system meeting the objects and goals set therefor. Those skilled in the art will appreciate that the embodiments shown in the drawings and described in the accompanying text are merely examples of the invention and that other embodiments, incorporating modifications and changes therein and including combinations of foregoing embodiments, fall within the scope of the invention.

Thus, for example, although the figures and corresponding text hereof are principally directed to embodiments employing skateboards, the teachings hereof may be utilized for identifying other feats of motion of the user alone or in connection with other objects. An enumeration of example such objects is provided elsewhere herein.

In view of the foregoing, what we claim is:

1. A system for skateboarding, comprising
    A. a skateboard,
    B. a sensing device that is attached or otherwise coupled to the skateboard and that measures a physical characteristic of it and/or of its environment,
    C. an audio output device,
    D. a digital data processor that is communicatively coupled to the audio output device and the sensor, wherein the digital data processor drives the audio output device to effect one or more selected sounds and, further, monitors the sensing device to identify operator actions in response to those sounds and drives the audio output device to effect still further sounds based on those actions,
    E. the digital data processor drives the audio output to effect a virtual sound space, and
    F. the digital data processor drives the audio output to effect the virtual sound space in which at least one of players, characters, obstacles, scenery, an actor representing the skateboard operator, his/her game status, and skateboard movements (or other interactions) with the foregoing are represented to the operator by sounds.

2. The system of claim 1, in which the operator effects those movements and interactions by moving and/or performing tricks (or feats) with that skateboard in the real and physical space surrounding him/her.

3. The system of claim 1, in which the digital data processor drives the audio output to effect the virtual sound space as a function of scripts, guidelines, programming or other rules (collectively, "rules") and/or data that define (a) define a game, sport, entertainment activity, training exercise or other endeavor for which the skateboard is being used.

4. The system of claim 1, in which the digital data processor drives the audio output device to effect sounds of approval/disapproval or degrees thereof.

5. The system of claim 1, in which the digital data processor drives the audio output device to simulate sounds of an object near or far from the operator and/or moving relative thereto.

6. The system of claim 1, in which the digital data processor determines whether the operator moved in a prescribed manner relative to the simulated object.

7. The system of claim 1, in which the digital data processor determines whether the operator performed a trick or other action on the skateboard that is interpreted as touching, capturing, shooting, freeing, or taking some other action with respect to the simulated object.

8. The system of claim 1, in which the digital data processor drives the audio output device simulate sounds of an object that is imaginary.

9. The system of claim 1, in which the digital data processor drives the audio output device simulate sounds of an object whose position and/or actions are based on a real-world object.

10. The system of claim 1, in which the digital data processor drives the audio output to effect the virtual sound space as a function of scripts, guidelines, programming or other rules (collectively, "rules") and/or data.

11. The system of claim 10, in which the operator effects those movements and interactions by moving and/or performing tricks (or feats) with that skateboard in the real and physical space surrounding him/her.

12. The system of claim 1, in which the digital data processor drives the audio output to effect sounds defining at least a portion of the virtual sound space in a vicinity of an actor representing the skateboard and/or its operator.

13. The system of claim 12, in which the digital data processor drives the audio output to effect sounds reflecting the skateboard operator's (and/or the skateboard's) interaction with that virtual sound space.

14. The system of claim 1, in which the digital data processor drives the audio output to effect a voice.

15. The system of claim 14, in which the voice commands the skateboard operator to take a particular action.

16. A system for skateboarding, surfboarding, snowboarding, skiing, rollerblading, or other game or sport and/or training therefor, comprising
   A. any of a skateboard, surfboard, snowboard, ski, rollerblade boot, or other apparatus for game or sport (collectively, "game/sport object")
   B. a sensing device that is attached or otherwise coupled to the game/sport object and that measures a physical characteristic of it and/or of its environment,
   C. an audio output device, and
   D. a digital data processor that is communicatively coupled to the audio output device and the sensor, wherein the digital data processor drives the audio output device to effect one or more selected sounds and, further, monitors the sensing device to identify operator actions in response to those sounds and drives the audio output device to effect still further sounds based on those actions,
   E. the digital data processor drives the audio output to effect a virtual sound space, and
   F. the digital data processor drives the audio output to effect the virtual sound space in which at least one of players, characters, obstacles, scenery, an actor representing the game/sports object operator, his/her game status, and game/sports object movements (or other interactions) with the foregoing are represented to the operator by sounds.

17. A system for game, sports, entertainment or other endeavor, comprising
   A. an object,
   B. a sensing device that is attached or otherwise coupled to the object and that measures a physical characteristic of it and/or of its environment,
   C. an audio output device, and
   D. a digital data processor that is communicatively coupled to the audio output device and the sensor, wherein the digital data processor drives the audio output device to effect one or more selected sounds and, further, monitors the sensing device to identify operator actions in response to those sounds and drives the audio output device to effect still further sounds based on those actions,
   E. the digital data processor drives the audio output to effect virtual sound space, and
   F. the digital data processor drives the audio output to effect the virtual sound space in which at least one of players, characters, obstacles, scenery, an actor representing the object operator, his/her game status, and object movements (or other interactions) with the foregoing are represented to the operator sounds.

* * * * *